(12) United States Patent
Selvaraj et al.

(10) Patent No.: US 12,152,238 B2
(45) Date of Patent: Nov. 26, 2024

(54) GENE EDITING SYSTEM FOR EDITING THE ARYLSULFATASE A (ARSA) GENE

(71) Applicant: Eberhard-Karls-Universität Tübingen Universitätsklinikum, Tübingen (DE)

(72) Inventors: Justin Antony Selvaraj, Weil am Rhein (DE); Markus Mezger, Tübingen (DE)

(73) Assignee: Eberhard-Karls-Universität Tübingen Universitätsklinikum, Tübingen (DE)

( * ) Notice: Subject to any disclaimer, the term of this patent is extended or adjusted under 35 U.S.C. 154(b) by 0 days.

(21) Appl. No.: 18/060,193

(22) Filed: Nov. 30, 2022

(65) Prior Publication Data

US 2024/0175011 A1    May 30, 2024

(51) Int. Cl.
| | | |
|---|---|---|
| *C12N 15/11* | (2006.01) | |
| *A61K 38/00* | (2006.01) | |
| *A61P 3/00* | (2006.01) | |
| *C12N 9/22* | (2006.01) | |

(52) U.S. Cl.
CPC ............... *C12N 15/11* (2013.01); *A61P 3/00* (2018.01); *C12N 9/22* (2013.01); *A61K 38/00* (2013.01); *C12N 2310/20* (2017.05); *C12N 2800/80* (2013.01)

(58) Field of Classification Search
CPC ...... C12N 15/11; C12N 2310/20; C12N 9/22; C12N 2800/80; A61P 3/00; A61K 38/00
See application file for complete search history.

(56) References Cited

U.S. PATENT DOCUMENTS

| | | | |
|---|---|---|---|
| 8,697,359 B1 * | 4/2014 | Zhang ................. | C12Q 1/68 435/6.13 |
| 2015/0232883 A1 * | 8/2015 | Dahlman ............. | C12N 15/907 435/320.1 |

OTHER PUBLICATIONS

"ARSA CRISPR guide RNA, arylsulfatase A CRISPR guide RNA [human]," retrieved from <https://www.genscript.com/gRNA-detail/410/ARSA-CRISPR-guide-RNA.html> on Jan. 3, 2024 (Year: 2015).*
Shaimardanova, A. et al. "Metachromatic Leukodystrophy. Diagnosis, Modeling, and Treatment Approaches." Frontiers in Medicine. 7:576221. (Year: 2020).*

* cited by examiner

*Primary Examiner* — Suzanne M Noakes
*Assistant Examiner* — Ciara A McKnight
(74) *Attorney, Agent, or Firm* — Knobbe, Martens, Olson & Bear, LLP

(57) ABSTRACT

The present invention relates to a gene editing system for editing the arylsulfatase A (ARSA) gene, polynucleotides, sgRNA molecules and repair templates which may form parts of the gene editing system, vectors and host cells incorporating said nucleic acid molecules, a pharmaceutical composition, and kits. It also relates to a method of gene editing the arylsulfatase A (ARSA) gene in a cell or a subject, and to a method of treating a disease or disorder associated with functional deficiency of the ARSA enzyme in a subject.

15 Claims, 23 Drawing Sheets

Specification includes a Sequence Listing.

D

E

E

F

G

H

SEQUENCE LISTING

```
Sequence total quantity: 32
SEQ ID NO: 1            moltype = RNA   length = 23
FEATURE                 Location/Qualifiers
source                  1..23
                        mol_type = other RNA
                        organism = synthetic construct
SEQUENCE: 1
cgcggtgccc ccatggacat ggg                                           23

SEQ ID NO: 2            moltype = RNA   length = 23
FEATURE                 Location/Qualifiers
source                  1..23
                        mol_type = other RNA
                        organism = synthetic construct
SEQUENCE: 2
ctttccgata ccgcagaccc agg                                           23

SEQ ID NO: 3            moltype = RNA   length = 23
FEATURE                 Location/Qualifiers
source                  1..23
```

```
                            mol_type = other RNA
                            organism = synthetic construct
SEQUENCE: 3
agtcacttgg cgctgaccag cgg                                               23

SEQ ID NO: 4               moltype = RNA   length = 23
FEATURE                    Location/Qualifiers
source                     1..23
                           mol_type = other RNA
                           organism = synthetic construct
SEQUENCE: 4
cccggaccca aatactcccc gac                                               23

SEQ ID NO: 5               moltype = RNA   length = 23
FEATURE                    Location/Qualifiers
source                     1..23
                           mol_type = other RNA
                           organism = synthetic construct
SEQUENCE: 5
cgagggtct gtcccaagag agg                                                23

SEQ ID NO: 6               moltype = DNA   length = 2249
FEATURE                    Location/Qualifiers
source                     1..2249
                           mol_type = other DNA
                           organism = synthetic construct
SEQUENCE: 6
tggtcagcgc caagtgactt acgcccccga ccctgagccc ggaccgctag gcgaggagga       60
tcagatctcc gctcgagaat ctgaaggtgc cctggtcctg gaggagttcc gtcccagccc     120
gcggtctccc ggtactgtcg ggccccggcc ctctggagct tcaggaggcg gccgtcaggg     180
tcggggagta tttgggtccg gggtctcagg aagggcggc gcctgggtct gcggtatcgg      240
aaagagcctg ctggagccaa gtagccctcc ctctcttggg acagacccct cggtaacatg     300
agcatgggag cccctagatc tctgctgctg gctctgctg ctggactggc agttgccaga      360
cctcctaaca tcgtgctgat cttcgccgac atctccggct atggcgatct gggctgttac     420
ggacacccca gcagccaccac acctaacctg gatcaacttg ccgctggcgg cctgagattc     480
accgatttct acgtgcccgt gtctctgtgc acccccttcta gagctgctct gctgacaggc     540
agactccctg tgcggatggg aatgtatcct ggcgtgctgg tgccttccag tagaggcgga     600
ctgcctctgg aagaagtgac agttgccgaa gtgctggccg ccagaggata tctgactggc     660
atggccggaa agtggcacct cggagttgga cctgaaggcg cttttctgcc tcctcaccag     720
ggcttccacc ggtttctggg catccccttac tctcacgatc agggccctg ccagaacctg     780
acctgttttc ctcctgccac accttgcgac ggcggctgtg atcaaggact ggtgcctatt     840
cctctgctgg ccaacctgag cgtggaagct caacctcctt ggctgccagg actggaagcc     900
cggtatatgg ccttcgctca cgacctgatg gccgacgtc agagacagga cagaccattc     960
ttcctgtact acgccagcca ccacacacac taccctcagt ttagcggcca gagcttcgcg    1020
gagagatctg gcagaggacc tttcggcgac agcctgatgg aactggatgc cgctgtgggc    1080
acactgatga cagcaattgg agatctggga ctgctgaaag acactggt catcttcacc      1140
gccgcaaacg gccccgagac aatgagaatg tctagagacg gcgtagcgg cctgctgaga     1200
tgtggcaagg gcaccacata tgaaggcggc gtcagagaac ctgctctggc cttttggcct     1260
ggccatattg ctccaggcgt gacacgag ctggcctctt ctctggatct gctgcctaca       1320
ctggcagctc ttgctggtgc tcccctgcct aatgtgaccc tggatggctt cgatctgagc     1380
ccactgctgc tcggcacagg caagtctcca agacagagcc tgttcttcta ccctagctac     1440
cccgatgaag tgcggggagt gtttgccgtg cggaccggaa agtataaggc ccacttcttc     1500
acccaaggca cgcgccactc tgacaccaca gctgatcctg cttgtcacgc cagctctagc     1560
ctgacagccc atgaacctcc actgctgtac gacctgagca aggaccccgg cgagaactac     1620
aatctgcttg gcggagttgc cggcgctaca cctgaagttc tgcaggccct gaaacagtcc     1680
cagctgctga aagcccagct ggacgctgcc gtgacatttg gacctagtca ggtggccaga     1740
ggcgaggatc ctgctctgca gatctgttgt caccctggct gcacacccag acctgcctgc     1800
tgtcattgtc ctgatcctca cgcctgaaac ttgtttatg cagcttataa tggttacaaa     1860
taaagcaata gcatcacaaa tttcacaaat aaagcatttt tttcactgca ttctagttgt     1920
ggtttgtcca aactcatcaa tgtatcttat ccatggggc accgcggtcc ctcctcctgg     1980
ccctggctgc tggcctggcc gttgcccgtc gcccaacat cgtgctgatc tttgccgacg      2040
acctcggcta tggggacctg gctgctatg ggcaccccag ctctaccact cccaacctgg      2100
accagctggc ggcgggaggg ctgcggttca cagacttcta cgtgcctgtg tctctgtgca     2160
caccctctag gtaaagaggg ggccgcgcct cttccccgcc ccgaccctcc atcccttccc     2220
tcccaatgga ttgcaggggg gcgggaaaa                                       2249

SEQ ID NO: 7               moltype = DNA   length = 1439
FEATURE                    Location/Qualifiers
source                     1..1439
                           mol_type = other DNA
                           organism = synthetic construct
SEQUENCE: 7
tggtcagcgc caagtgactt acgcccccga ccctgagccc ggaccgctag gcgaggagga       60
tcagatctcc gctcgagaat ctgaaggtgc cctggtcctg gaggagttcc gtcccagccc     120
gcggtctccc ggtactgtcg ggccccggcc ctctggagct tcaggaggcg ccgtcaggg      180
tcggggagta tttgggtccg gggtctcagg aagggcggc gcctgggtct gcggtatcgg      240
aaagagcctg ctggagccaa gtagccctcc ctctcttggg acagacccct cggtaacatg     300
gtgagcaagg gcgaggagct gttcaccggg gtggtgccca tcctggtcga gctggacggc     360
gacgtaaacg gccacaagtt cagcgtgtcc ggcgagggcg agggcgatgc cacctacggc     420
```

```
aagctgaccc tgaagttcat ctgcaccacc ggcaagctgc ccgtgccctg gcccacccic   480
gtgaccaccc tgacctacgg cgtgcagtgc ttcagccgct accccgacca catgaagcag   540
cacgacttct tcaagtccgc catgcccgaa ggctacgtcc aggagcgcac catcttcttc   600
aaggacgacg gcaactacaa gacccgcgcc gaggtgaagt tcgagggcga caccctggtg   660
aaccgcatcg agctgaaggg catcgacttc aaggaggacg gcaacatcct ggggcacaag   720
ctggagtaca actacaacag ccacaacgtc tatatcatgg ccgacaagca gaagaacggc   780
atcaaggtga acttcaagat ccgccacaac atcgaggacg gcagcgtgca gctcgccgac   840
cactaccagc agaacacccc catcggcgac ggccccgtgc tgctgcccga caaccactac   900
ctgagcaccc agtccgccct gagcaaagac cccaacgaga agcgcgatca catggtcctg   960
ctggagttcg tgaccgccgc cgggatcact ctcggcatgg acgagctgta caagtaaaac  1020
ttgtttattg cagcttataa tggttacaaa taaagcaata gcatcacaaa tttcacaaat  1080
aaagcatttt tttcactgca ttctagttgt ggtttgtcca aactcatcaa tgtatcttat  1140
ccatggggggc accgcggtcc ctcctcctgg ccctggctgt tggcctggcc gttgcccctc  1200
cgcccaacat cgtgctgatc tttgccgacg acctcggcta gggctgctatg           1260
ggcaccccag ctctaccact cccaacctgg accagctggc ggcgggaggg ctgcggttca  1320
cagacttcta cgtgcctgtg tctctgtgca caccctctag gtaaagaggg ggcccgcgcct 1380
cttccccgcc ccgaccctcc atccctttcc tcccaatgga ttgcagggggg gcgggaaaa  1439

SEQ ID NO: 8              moltype = DNA   length = 20
FEATURE                   Location/Qualifiers
source                    1..20
                          mol_type = other DNA
                          organism = synthetic construct
SEQUENCE: 8
ctcttgggac agacccctcg                                                20

SEQ ID NO: 9              moltype = DNA   length = 20
FEATURE                   Location/Qualifiers
source                    1..20
                          mol_type = other DNA
                          organism = synthetic construct
SEQUENCE: 9
gggtctgcgg tatcggaaag                                                20

SEQ ID NO: 10             moltype = DNA   length = 20
FEATURE                   Location/Qualifiers
source                    1..20
                          mol_type = other DNA
                          organism = synthetic construct
SEQUENCE: 10
ctggtcagcg ccaagtgact                                                20

SEQ ID NO: 11             moltype = DNA   length = 20
FEATURE                   Location/Qualifiers
source                    1..20
                          mol_type = other DNA
                          organism = synthetic construct
SEQUENCE: 11
gtcggggagt atttgggtcc                                                20

SEQ ID NO: 12             moltype = DNA   length = 20
FEATURE                   Location/Qualifiers
source                    1..20
                          mol_type = other DNA
                          organism = synthetic construct
SEQUENCE: 12
atgtccatgg gggcaccgcg                                                20

SEQ ID NO: 13             moltype = DNA   length = 21
FEATURE                   Location/Qualifiers
source                    1..21
                          mol_type = other DNA
                          organism = synthetic construct
SEQUENCE: 13
ggaacccccta gtgatggagt t                                             21

SEQ ID NO: 14             moltype = DNA   length = 16
FEATURE                   Location/Qualifiers
source                    1..16
                          mol_type = other DNA
                          organism = synthetic construct
SEQUENCE: 14
cggcctcagt gagcga                                                    16

SEQ ID NO: 15             moltype = DNA   length = 21
FEATURE                   Location/Qualifiers
source                    1..21
                          mol_type = other DNA
                          organism = synthetic construct
```

```
SEQUENCE: 15
cactccctct ctgcgcgctc g                                                  21

SEQ ID NO: 16           moltype = DNA   length = 20
FEATURE                 Location/Qualifiers
source                  1..20
                        mol_type = other DNA
                        organism = synthetic construct
SEQUENCE: 16
cgcaagggtc acaggtcacg                                                    20

SEQ ID NO: 17           moltype = DNA   length = 20
FEATURE                 Location/Qualifiers
source                  1..20
                        mol_type = other DNA
                        organism = synthetic construct
SEQUENCE: 17
aggaaaggga tggagggtcg                                                    20

SEQ ID NO: 18           moltype = DNA   length = 20
FEATURE                 Location/Qualifiers
source                  1..20
                        mol_type = other DNA
                        organism = synthetic construct
SEQUENCE: 18
tctacccgtc ctacccagac                                                    20

SEQ ID NO: 19           moltype = DNA   length = 20
FEATURE                 Location/Qualifiers
source                  1..20
                        mol_type = other DNA
                        organism = synthetic construct
SEQUENCE: 19
cagagccctg ggtgaagaag                                                    20

SEQ ID NO: 20           moltype = DNA   length = 20
FEATURE                 Location/Qualifiers
source                  1..20
                        mol_type = other DNA
                        organism = synthetic construct
SEQUENCE: 20
gctgtgcgga ctggaaagta                                                    20

SEQ ID NO: 21           moltype = DNA   length = 20
FEATURE                 Location/Qualifiers
source                  1..20
                        mol_type = other DNA
                        organism = synthetic construct
SEQUENCE: 21
gcacaggcaa gtctccaaga                                                    20

SEQ ID NO: 22           moltype = DNA   length = 20
FEATURE                 Location/Qualifiers
source                  1..20
                        mol_type = other DNA
                        organism = synthetic construct
SEQUENCE: 22
tatactttcc ggtccgcacg                                                    20

SEQ ID NO: 23           moltype = DNA   length = 20
FEATURE                 Location/Qualifiers
source                  1..20
                        mol_type = other DNA
                        organism = synthetic construct
SEQUENCE: 23
atgaagtgcg gggagtgttt                                                    20

SEQ ID NO: 24           moltype = DNA   length = 22
FEATURE                 Location/Qualifiers
source                  1..22
                        mol_type = other DNA
                        organism = synthetic construct
SEQUENCE: 24
atccagcgta ctccaaagat tc                                                 22

SEQ ID NO: 25           moltype = DNA   length = 19
FEATURE                 Location/Qualifiers
source                  1..19
                        mol_type = other DNA
```

```
                        organism = synthetic construct
SEQUENCE: 25
tgaaacccag acacatagc                                                     19

SEQ ID NO: 26           moltype = DNA  length = 22
FEATURE                 Location/Qualifiers
source                  1..22
                        mol_type = other DNA
                        organism = synthetic construct
SEQUENCE: 26
agaatggaaa gtcaaatttc ct                                                 22

SEQ ID NO: 27           moltype = DNA  length = 20
FEATURE                 Location/Qualifiers
source                  1..20
                        mol_type = other DNA
                        organism = synthetic construct
SEQUENCE: 27
tggctgtgat acaaagcggt                                                    20

SEQ ID NO: 28           moltype = DNA  length = 20
FEATURE                 Location/Qualifiers
source                  1..20
                        mol_type = other DNA
                        organism = synthetic construct
SEQUENCE: 28
ggaaacaacc aggcaaagag                                                    20

SEQ ID NO: 29           moltype = DNA  length = 21
FEATURE                 Location/Qualifiers
source                  1..21
                        mol_type = other DNA
                        organism = synthetic construct
SEQUENCE: 29
gatgaagaaa ctaaggcacc g                                                  21

SEQ ID NO: 30           moltype = DNA  length = 20
FEATURE                 Location/Qualifiers
source                  1..20
                        mol_type = other DNA
                        organism = synthetic construct
SEQUENCE: 30
cactgcattc tagttgtggt                                                    20

SEQ ID NO: 31           moltype = DNA  length = 19
FEATURE                 Location/Qualifiers
source                  1..19
                        mol_type = other DNA
                        organism = synthetic construct
SEQUENCE: 31
ggtacatgcc catccgaac                                                     19

SEQ ID NO: 32           moltype = DNA  length = 21
FEATURE                 Location/Qualifiers
source                  1..21
                        mol_type = other DNA
                        organism = synthetic construct
SEQUENCE: 32
gtccaaactc atcaatgtat c                                                  21
```

GENE EDITING SYSTEM FOR EDITING THE ARYLSULFATASE A (ARSA) GENE

FIELD OF THE INVENTION

The present invention relates to a gene editing system for editing the arylsulfatase A (ARSA) gene, polynucleotides, sgRNA molecules and repair templates which may form parts of the gene editing system, vectors and host cells incorporating said nucleic acid molecules, a pharmaceutical composition, and kits. It also relates to a method of gene editing the arylsulfatase A (ARSA) gene in a cell or a subject, and to a method of treating a disease or disorder associated with functional deficiency of the ARSA enzyme in a subject.

REFERENCE TO SEQUENCE LISTING

The present application is being filed along with a Sequence Listing in electronic format. The Sequence Listing is provided as a file entitled 59621774_1.XML, created and last modified on May 29, 2024, which is 34,904 bytes in size. The information in the electronic format of the Sequence Listing is incorporated herein by reference in its entirety.

BACKGROUND OF THE INVENTION

Metachromatic leukodystrophy (MLD; OMIM:250100) is a rare inherited lysosomal storage disorder caused by mutations in the arylsulfatase A (ARSA) gene, which result in a functional deficiency of the ARSA enzyme. The lack of ARSA enzyme leads to impaired metabolism of sulfatides, which accumulate in the lysosomes of cells of the central and peripheral nervous system. The lysosomal storage of sulfatide leads to progressive demyelination and neurodegeneration. The clinical manifestations of the disease are characterized by developmental stagnation followed by the loss of abilities in motor function, language, and cognition.

MLD is classified into three clinical forms according to age at disease onset—a late infantile (50-60%), a juvenile (20-30%), and an adult form (20-30%)—with age at onset and type of first symptoms determining the course of the disease, which is most rapid in the early-onset forms. Although MLD is an orphan disease, it is a common disorder among leukodystrophies, with a frequency rate of 1 in 40,000-160,000 worldwide. Nonetheless, the disease incidence is estimated to be higher in some ethnic groups such as Habbanite-Jews (1 in 75), Navajo Indian (1 in 2,500) and Israeli Arabs (1 in 8,000).

As of today, several therapeutic approaches, including allogeneic hematopoietic stem cells transplantation (allogeneic-HSCT), enzyme replacement therapy, umbilical cord transplantation, and lentiviral (LV)-based gene therapy (autologous-HSCT), have been explored for the treatment of MLD. The rationale behind HSCT for MLD is based on a phenomenon known as "cross-correction", in which the healthy myeloid precursors migrate into the brain as microglial cells and secrete ARSA that will be assimilated by deficient brain cells, including oligodendrocytes, and will improve the sulfatide metabolism within neurons.

Allogeneic HSCT has found to be beneficial in MLD patients presenting with the juvenile form only when administered in a pre-symptomatic or early stage, but it is not considered to be efficient in the late-infantile disease type; Groeschel et al. Long-term outcome of allogeneic hematopoietic stem cell transplantation in patients with juvenile metachromatic leukodystrophy compared with nontransplanted control patients. JAMA Neurol 2016; 73:1133-1140. DOI: 10.1001/jama-neurol.2016.2067. Moreover, allogeneic-HSCT presents clinical risks, including increased chance of infections due to immune suppression, graft-versus-host disease, and reduced survival rate in cases where a suitable donor is unavailable. Enzyme replacement therapy in Phase I/II trials indicates low success only when given intrathecally.

A new treatment modality was developed that combined HSCT and gene therapy, where autologous HSPCs were transduced ex vivo with an ARSA-encoding LV vector. A preclinical study using LV-modified autologous HSPCs showed the rescue of neuropathological damage in a MLD mouse model and resulted in a human clinical trial. The autologous LV gene therapy approach resulted in clinical benefit in treated children with early-onset forms of MLD when administered in a pre-symptomatic stage, and showed prevention of clinical deterioration and demyelination, as well as reconstitution of ARSA enzyme activity in the cerebrospinal fluid (CSF) and peripheral leukocytes; Sessa et al. Lentiviral haemopoietic stem-cell gene therapy in early-onset metachromatic leukodystrophy: an ad-hoc analysis of a non-randomised, open-label, phase ½ trial. Lancet 2016; 388:476-487. DOI: 10.1016/S0140-6736(16)30374-9.

In December 2020, the European Medical Agency granted marketing authorization for the autologous LV gene therapy (Libmeldy) developed by Orchard Therapeutics. Despite the positive clinical data in these studies, the use of random and non-targeted integration of ARSA-expressing lentivirus resulted in more than 36,000 unique integration sites (UIS) in treated patients and more than 2,300 UIS in preclinical models. These integrations sites are reported to be polyclonal in nature, as the 9-year follow-up did not show any cancer development. However, this fact forewarns of the possibility of insertional mutagenesis.

Earlier retroviral gene therapy trials for the treatment of other inherited diseases reported treatment-related leukemogenesis and genotoxicity.

Against this background it is an object underlying the invention to provide tools and methods useful for addressing ARSA-associated disorders or diseases, such as MLD, where the disadvantages of alternative approaches are avoided or at least alleviated.

SUMMARY

This object is achieved by a gene editing system for editing the arylsulfatase A (ARSA) gene, comprising:
  (a) at least one single guide RNA (sgRNA) molecule and/or a nucleic acid molecule encoding said at least one gRNA, and
  (b) at least one RNA-guided endonuclease molecule or fragment thereof and/or a nucleic acid molecule encoding said at least one RNA-guided endonuclease or fragment thereof, wherein said sgRNA is configured to guide the RNA-guided endonuclease molecule or fragment thereof to a target region of the ARSA gene.

According to the invention a "nucleic acid" includes any kind of biopolymers composed of nucleotides, such as deoxyribonucleic acid (DNA) and ribonucleic acid (RNA).

According to the invention "gene editing" generally refers to genetic engineering where nucleic acid, in particular deoxyribonucleic acid (DNA), preferably genomic DNA, is modified, e.g., by nucleotide deletion, insertion and/or replacement etc. in a target specific manner. It also includes cleaving of phosphodiester bonds within a nucleic acid in a targeted manner. The modification includes, in an embodiment if the invention, the disruption or/and inactivation of the nucleic acid or DNA, and/or a gene encoded thereon.

Accordingly, editing the arylsulfatase A (ARSA) gene refers to the targeted modification of the arylsulfatase A (ARSA) gene, e.g., the ARSA gene located on the DNA of a genome of a subject, which, in an embodiment of the invention, results in the disruption or/and inactivation of the ARSA gene.

The ARSA gene encodes the arylsulfatase A, an enzyme that breaks down sulfatides, namely cerebroside 3-sulfate into cerebroside and sulfate. According to the invention the ARSA gene of mammals, in particular humans (OMIM: 607574; UniProt: P15289), is preferred. Human arylsulfatase A is a dimer of the entire 489 amino acid long chain, or a dimer of the complex of the two fragments, which are 426 and 60 amino acids long.

According to the invention an "RNA-guided endonuclease" refers to an enzyme which is directed to a polynucleotide chain by a specific RNA molecule or a guide RNA, e.g., a single guide RNA (sgRNA), where it cleaves phosphodiester bonds. Included are single-strand and double-strand endonucleases. Suitable RNA-guide endonucleases include, without being restricted thereto, CRISPR associated protein 9, 12, 3 (Cas9, Cas12, Cas3) etc.

A "fragment" of an RNA-guided endonuclease refers to a part or section or a domain of the entire enzyme having RNA-guided endonuclease activity. I.e., a fragment can differ from the entire enzyme, e.g., by at least one or more amino acid residues, but still retains functional endonuclease activity. Functional activity of a domain or fragment of a naturally occurring RNA-guided exonuclease described herein can be tested using functional assays for endonuclease activity known in the art. Using a fragment instead of an entire full-length enzyme can result in a higher expression level, increased enzymatic activity, simplifications in the formulation into a pharmaceutical composition, and finally lower production efforts and costs.

According to the invention a "single guide RNA (sgRNA)" refers to a piece of RNA that functions as a guide for the RNA-guided endonuclease, which it forms a complex with. The sgRNA is designed to specifically bind to or in close vicinity to the ARSA gene on the genomic DNA of a subject, e.g., a mammal or human, thereby guiding the RNA-guided endonuclease to a target region of the latter. The design of the sgRNA involves the incorporation of nucleotides resulting in a sequence which is complementary or at least essentially complementary to the nucleotide sequence of the target region, or a section thereof. A typical sgRNA has a length of approx. 17-24 base pairs but can be longer or shorter. In an embodiment of the invention where Cas9 is used as the RNA-guided endonuclease the desired target sequence of the splicing site must precede the so-called protospacer adjacent motif (PAM) which is a short DNA sequence usually 2-6 base pairs in length that follows the DNA region targeted for cleavage by the gene editing system.

"At least one" means, according to the invention, one, two, three, four, etc. . . . E.g., at least one gRNA not only means one gRNA but also include more than one, e.g., two or more gRNA molecules. Such a practice exists in CRISPR technologies where two sgRNA molecules are used to excise a specific part out of the genome and insert the desired sequence.

The terms "complementary" and "essentially complementary" in the present description can be used in relation to the match base pairs of the gRNA and the target sequence. According to the invention "essentially complementary" means that a polynucleotide strand is designed to hybridize (generally under physiological conditions such as those found in a living plant or animal cell) to the target region or to a fragment of the target region; one of skill in the art would understand that such hybridization does not necessarily require 100% sequence complementarity.

The inventors have realized that with the gene editing system according to the invention the ARSA gene, preferably a mutated, functionally deficient ARSA gene as found with metachromatic leukodystrophy (MLD), can be edited, preferably inactivated and/or replaced by a non-mutated ARSA gene, in a targeted manner. Surprisingly, the gene editing system according to the invention allows a so-called mutation-agnostic or mutation-independent editing of the ARSA gene, meaning that the specific mutation need not to be known as the system according to the invention is capable of editing every mutation in the ARSA gene. This advantage of the system according to the invention makes the latter particularly suitable as a therapeutic tool for the treatment and/or prophylaxis of ARSA-associated diseases or disorders, such as MLD, for which more than 200 different ARSA mutations are known to cause the disease.

In an embodiment of the invention the edited ARSA gene comprises at least one mutation resulting in a functional deficiency or low expression of the ARSA enzyme.

This measure has the advantage that the gene editing system according to the invention is adapted for the targeted treatment of ARSA-associated diseases or disorders, such as MLD, which is characterized by mutations in the ARSA gene resulting in a functional deficiency of the ARSA enzyme.

In another embodiment of the gene editing system of the invention said RNA-guided endonuclease molecule or fragment thereof, when associated with the target region, causes a double-strand break within the target region.

This measure has the advantage that the ARSA gene on the genomic DNA is effectively and permanently knocked-down or disrupted resulting in a lack of the ARSA enzyme, such as the functionally deficient ARSA enzyme as can be observed in ARSA-associated diseases or disorders, such as MLD. In an alternative embodiment, the RNA-guided endonuclease molecule or fragment thereof causes a single-strand break, i.e. nick, within the target region in the ARSA gene.

In yet another embodiment of the invention said target region for the sgRNA and/or RNA-guided endonuclease molecule or fragment thereof is located within the untranslated region (UTR) of the ARSA gene, preferably within the 5' UTR of the ARSA gene, or within exon 1 of the ARSA gene.

The inventors have found that these target regions within the ARSA gene are particularly specific and enable the design and use of sgRNA molecules with few off-targets. At the same time, it ensures that the expression of the addressed ARSA gene is selectively and effectively modified, preferably inhibited or even knocked down.

In still another embodiment of the invention said RNA-guided endonuclease molecule is a Cas9 molecule.

This measure has the advantage that such an RNA-guided endonuclease is used, which is particularly suitable for the purposes of the invention. Cas9 (CRISPR associated protein 9, formerly called Cas5, Csn1, or Csx12) is a 160 kilodalton protein which has been proven to induce site-directed strand breaks in DNA in many genetic engineering applications.

Cas9 is a dual RNA-guided DNA endonuclease enzyme associated with the Clustered Regularly Interspaced Short Palindromic Repeats (CRISPR) system. Cas9 can cleave nearly any sequence complementary to the sgRNA. Because the target specificity of Cas9 stems from the guide RNA: DNA complementarity and not from modifications to the protein itself (like TALENs and zinc fingers), engineering Cas9 to target new DNA is straightforward in the light of the current specification. The induction of DNA strand breaks by Cas9 can lead to the inactivation of the splicing site or the introduction of heterologous sequences through non-homologous end joining and homologous recombination, respectively.

Preferably said Cas9 is selected from the group consisting of: *Streptococcus pyogenes* Cas9 (SpCas9), *Streptococcus pyogenes* high fidelity Cas9 (HiFi Cas9), *Streptococcus pyogenes* enhanced specificity Cas9 (eSpCas9), hyper-accurate Cas9 (HypaCas9), *Neisseria meningitides* Cas9 (Nme2Cas9), and *Staphylococcus auricularis* Cas9 (SauriCas9).

The measure has the advantage that such Cas9 enzymes are used which achieve particularly good results in the invention. While the use of standard SpCas9 has been demonstrated in numerous applications to ensure effective editing activity Nme2Cas9 and SauriCas9 have the advantage of being small Cas9 orthologous which are active in mammalian cells and which can be packed in AAV particles; see Edraki et al. (2019), A compact, high-accuracy Cas9 with a dinucleotide PAM for in vivo genome editing. Mol Cell 73: 714-726; Hu et al. (2020), A compact Cas9 ortholog from *Staphylococcus auricularis* (SauriCas9) expands the DNA targeting scope. PLOS Biol 18: e3000686. All aforementioned documents are incorporated herein by reference. Moreover, due to the permissive protospacer adjacent motif (PAM) requirements (N4CC for Nme2Cas9, NNGG for SauriCas9 and NGG for SpCas9) the availability of various Cas9 orthologues results in a higher flexibility in targeting defined DNA sequences. *Streptococcus pyogenes* high fidelity Cas9 (HiFi Cas9) has been described as an RNA-guided endonuclease molecule capable of reducing the number of off-targets compared to canonical Cas9.

In another preferred embodiment of the invention said sgRNA molecule comprises a nucleotide sequence selected from the group consisting of SEQ ID NO:1 (sgRNA-5), SEQ ID NO:2 (sgRNA-2), SEQ ID NO:3 (sgRNA-3), SEQ ID NO:4 (sgRNA-4), and SEQ ID NO:5 (sgRNA-1).

Hereby, such sgRNA molecules are used within a target region of the ARSA 5' UTR or in close proximity to the transcriptional start site, which are characterized by particularly few off-targets according to the knowledge of the inventors. Said specific sgRNA molecules were selected out of more than 50 different sgRNAs due to their low off-target activities. For example, only one off-target was found for sgRNA-5 in silico, and only between 3 and 10 off-targets for the remaining srRNA1-4. Side effects during therapeutic use of the system according to the invention are thus minimized.

As a convention, it is understood that all nucleotide sequences of the present disclosure are given in terms of DNA sequences. However, the sequences also include RNA sequences. The RNA sequence corresponding to a specified DNA sequence results from the fact that all thymines (T, t) are replaced by uracils (U, u). Such an exchange takes place in particular when reference is made to sgRNA molecules, but a DNA sequence is explicitly specified. This means, for example, that the nucleotide sequence SEQ ID NO: 1: CGCGGTGCCCCCATGGACATGGG specified in the form of DNA comprises the following RNA nucleotide sequence: CGCGGUGCCCCAUGGACAUGGG (SEQ ID NO: 33). The same applies to the nucleotide sequences of the remaining sgRNA molecules according to the invention.

In an embodiment of the invention said gene editing system further comprises (c) at least one repair template configured for the cellular expression of a functional ARSA enzyme.

The repair template is configured for the cellular expression of a functional ARSA enzyme. This means that the repair template carries the information, in particular in the form of the coding sequence, which serves to produce a functional, non-mutated ARSA enzyme by way of protein biosynthesis in a biological cell. The repair template can be integrated into the endogenous ARSA locus on DNA in a targeted manner—but not only randomly as in the art—using the so-called homology directed repair (HDR) pathway. This way, the wild-type copy number is maintained along with endogenous regulatory elements, preventing undesired integrations and overexpression. With this measure, the gene editing system according to the invention is extended by a component that ensures the provision of a functional ARSA enzyme after the, preferably genomic, endogenous and dysfunctional ARSA enzyme has been modified, in particular inhibited or knocked-down or replaced, by the complex of sgRNA and RNA-guided endonuclease and repair template. According to the invention, the repair template can be DNA, including cDNA, or RNA, preferably in form of an oligonucleotide, further preferably packed into a vector such as AAV, including AAV6.

In yet another embodiment of the invention said repair template comprises a nucleotide sequence having optimized codons for an expression in mammalian cells, preferably human cells. In embodiments of the invention, it may also or additionally contain an SV40 poly-A tail sequence and/or homology arms.

With this measure, the inventors make use of codon optimization, i.e., when coding the functional ARSA enzyme, such codons are used that allow the optimal translation of the template or production of the enzyme in the cell, e.g., a mammalian or human cell. The principle of codon optimization is generally well-known to the skilled person; see Fath et al. Multiparameter RNA and codon optimization: a standardized tool to assess and enhance autologous mammalian gene expression. PLOS One 2011; 6:e17596. DOI: 10.1371/journal.pone.0017596. This document is incorporated herein by reference. However, said technique is employed by the inventors for the very first time for the manufacturing of an ARSA repair template as a component of a gene editing system. The SV40 poly-A tail sequence (122 bp) prevents transcription of the mutated gene, and the homology arms (300 bp) enhance the HDR pathway.

In still another embodiment of the invention said repair template comprises the nucleotide sequence of SEQ ID NO:6 (ARSA-cDNA).

This measure provides a repair template that is particularly suitable according to the invention. It codes for a mutation-free, human ARSA enzyme and is characterized by codon optimization and thus particularly high translation efficiency. Furthermore, it contains the SV40 poly-A tail sequence (122 bp) to prevent transcription of the mutated gene, and 300 bp homology arms to enhance the HDR pathway. A targeted integration into the endogenous ARSA locus is hereby ensured.

In an embodiment of the invention, therefore, said ARSA gene is a human ARSA gene.

By this measure, the gene editing system according to the invention is advantageously adapted for use in human cells or in humans.

Another subject-matter of the invention relates to an isolated polynucleotide encoding the gene editing system according to the invention or at least any of its components. Further, another subject-matter of the invention is a vector, preferably a viral vector, comprising said isolated polynucleotide Another subject-matter of the invention relates to a host cell comprising said isolated polynucleotide or vector.

A polynucleotide, according to the invention, includes DNA (e.g., cDNA), and RNA, composed of 13, 20 or more nucleotide monomers covalently bonded in a chain. The nucleotides are linked by a 5'->3'-phosphodiester bond.

An "isolated" polynucleotide is a nucleotide sequence that, by the hand of man, exists apart from its native environment and is therefore not a product of nature. In this embodiment, the polynucleotide is "isolated". An isolated polynucleotide can exist in a purified form that is at least partially separated from at least some of the other components of the naturally occurring organism or virus, for example, the cell or viral structural components or other polypeptides or polynucleotides commonly found associated with the polypeptide or polynucleotide. In representative embodiments, the isolated is at least about 1%, 5%, 10%, 20%, 30%, 40%, 50%, 60%, 70%, 80%, 90%, 95%, or more pure.

Vectors according to the invention include any particle (e.g., plasmids, cosmids, Lambda phages) used as a vehicle in molecular cloning to artificially carry a foreign nucleic sequence—usually DNA—into another cell, where it can be replicated and/or expressed. Especially preferred are viral vectors, such as AAV vectors, e.g., AA6 vectors.

Host cells include a myriad of cell types, for example, including, but not limited to eukaryotic cells or prokaryotic cells. In some embodiments, the eukaryotic cell can be any eukaryotic cell from any eukaryotic organism. Non-limiting examples of eukaryotic organisms include mammals, insects, amphibians, reptiles, birds, fish, fungi, plants, and/or nematodes. In some embodiments, the cell is a mammalian cell. In some embodiments, the cell is a human cell. In some embodiments, the cell may be a CD34+ cell, especially a hematopoietic stem and progenitor cell (HSPC).

Methods of introducing a nucleic acid into a host cell are known in the art, and any known method can be used to introduce a nucleic acid (e.g., an expression construct) into a cell. Suitable methods include, include e.g., viral or bacteriophage infection, transfection, conjugation, protoplast fusion, polycation or lipid:nucleic acid conjugates, lipofection, electroporation, nucleofection, immunoliposomes, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like. In some embodiments, the composition may be introduced by mRNA delivery and ribonucleoprotein (RNP) complex delivery.

Another subject-matter of the invention is a pharmaceutical composition comprising at least one of the gene editing system, the isolated polynucleotides, the vector, or the host cell according to the invention, or combinations thereof.

The disclosure provides for pharmaceutical compositions comprising the gene editing system, isolated polynucleotide, vector, or host cell for editing the arylsulfatase A (ARSA) gene. The pharmaceutical composition may comprise about 1 ng to about 10 mg of DNA encoding the gene editing system, polynucleotide, vector, or host cell for editing the arylsulfatase A (ARSA) gene. For example, about 1 ng to about 100 ng, about 10 ng to about 250 ng, about 50 ng to about 500 ng, about 100 ng to about 750 ng, about 500 ng to about 1 mg, about 750 ng to about 2 mg, about 1 mg to about 5 mg, 2 mg to about 6 mg, about 3 mg to about 7 mg, about 4 mg to about 8 mg, about 5 mg to about 10 mg, or any value in between. The pharmaceutical compositions according to the present invention are formulated according to the mode of administration to be used. In cases where pharmaceutical compositions are injectable pharmaceutical compositions, they are aqueous, sterile-filtered and pyrogen free. An isotonic formulation is preferably used. Generally, additives for isotonicity may include sodium chloride, dextrose, mannitol, sorbitol, lactose, and any combinations of the foregoing. In some cases, isotonic solutions such as phosphate buffered saline are preferred. In some cases, the pharmaceutical compositions further comprise one or more stabilizers. Stabilizers include, but are not limited to, gelatin and albumin. In some embodiments, a vasoconstriction agent is added to the formulation.

The pharmaceutical composition may further comprise a pharmaceutically acceptable excipient. The pharmaceutically acceptable excipient may be functional molecules as vehicles, adjuvants, carriers, or diluents. The method of administration will dictate the type of carrier to be used. Any suitable pharmaceutically acceptable excipient for the desired method of administration may be used. The pharmaceutically acceptable excipient may be a transfection facilitating agent. The transfection facilitating agent may include surface active agents, such as immune-stimulating complexes (ISCOMS), Freund's incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents. The transfection facilitating agent may be a polyanion, polycation, including poly-L-glutamate (LGS), or lipid. The transfection facilitating agent may be poly-L-glutamate. The poly-L-glutamate may be present in the pharmaceutical composition at a concentration less than 6 mg/ml. The pharmaceutical composition may include transfection facilitating agent(s) such as lipids, liposomes, including lecithin liposomes or other liposomes known in the art, as a DNA-liposome mixture, calcium ions, viral proteins, polyanions, polycations, or nanoparticles, or other known transfection facilitating agents. Preferably, the transfection facilitating agent is a polyanion, polycation, including poly-L-glutamate (LGS), or lipid.

A still further subject-matter of the invention is a kit comprising at least one of the gene editing system, the isolated polynucleotide, the vector, or the host cell according to the invention, or combinations thereof.

The kit provided herein may be used for gene editing the arylsulfatase A (ARSA) gene. A "kit" is a combination of individual elements useful for carrying out the invention, wherein the elements are optimized for use together in the methods. The kits may also contain additional reagents, chemicals, buffers, reaction vials etc. which may be useful for carrying out the invention. The kit may comprise instructions for using the disclosed composition, polynucleotide, vector, or pharmaceutical composition for editing the arylsulfatase A (ARSA) gene. Instructions included in kits may be affixed to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions. Such kits unify all essential elements required to work the invention, thus minimizing the risk of errors. Therefore, such kits also allow semi-skilled laboratory staff to perform the invention.

Another subject-matter of the invention relates to a method of gene editing the arylsulfatase A (ARSA) gene in a biological cell or a subject, the method comprising contacting the cell or subject with at least one of the gene editing system, the isolated polynucleotide, the vector, the host cell, or the pharmaceutical composition according to the invention, or combinations thereof, in an amount sufficient to gene edit the ARSA gene.

The present disclosure provides for methods of in vivo and in vitro gene editing the arylsulfatase A (ARSA) gene. The method can include modulation of expression of an ARSA gene in a biological cell. The method can include modulation of expression of an ARSA gene in a subject. The method can include administering to the cell or subject the presently disclosed gene editing system, polynucleotide, vector, host cell, or pharmaceutical composition for gene editing of an ARSA gene. The method can include administering to the cell or subject a pharmaceutical composition comprising the same.

The invention also relates to a method of treating a disease or disorder associated with functional deficiency of the ARSA enzyme in a subject, preferably metachromatic leukodystrophy (MLD), the method comprising administering to the subject or a biological cell in the subject at least one of the gene editing system, the isolated polynucleotide, the vector, the host cell, or the pharmaceutical composition according to the invention, or combinations thereof, in an amount sufficient to gene edit the ARSA gene.

The disclosure provided above for the "host cell" according to the invention applies to the cell recited in the method according to the invention in the same manner.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

Another subject-matter of the invention relates to a single guide RNA (sgRNA) molecule configured to guide an RNA-guided endonuclease molecule or fragment thereof to a target region within an ARSA gene, wherein, in an embodiment, the ARSA gene comprises at least one mutation resulting in a functional deficiency or low expression of the ARSA enzyme, and, in a further embodiment, said target region is within the untranslated region (UTR) of the ARSA gene, preferably within the 5' UTR of the ARSA gene.

The invention also relates to a sgRNA molecule comprising a nucleotide sequence selected from the group consisting of: SEQ ID NO:1 (sgRNA-5), SEQ ID NO:2 (sgRNA-2), SEQ ID NO:3 (sgRNA-3), SEQ ID NO:4 (sgRNA-4), and SEQ ID NO:5 (sgRNA-1)

The invention further relates to a repair template configured for the cellular expression of a functional ARSA enzyme, wherein, in an embodiment, said repair template comprising a nucleotide sequence having optimized codons for an expression in mammalian cells, preferably human cells.

The invention also relates to a repair template comprising the nucleotide sequence of SEQ ID NO:6 (ARSA-cDNA). The repair template may by DNA, including cDNA, or RNA.

A yet further subject-matter of the invention is an isolated polynucleotide encoding the sgRNA molecule and/or the repair template according to the invention. The isolated polynucleotide may by DNA, including cDNA, or RNA.

Still a further subject-matter of the invention relates to an isolated polynucleotide comprising a nucleotide sequence selected from the group consisting of: SEQ ID NO:1 (sgRNA-5), SEQ ID NO:2 (sgRNA-2), SEQ ID NO:3 (sgRNA-3), SEQ ID NO:4 (sgRNA-4), SEQ ID NO:5 (sgRNA-1), and SEQ ID NO:6 (ARSA-cDNA).

Further subject-matters of the invention are a vector comprising said isolated polynucleotides and a host cell comprising said isolated polynucleotide and/or said vector.

Yet, a further subject-matter of the invention relates to a pharmaceutical composition comprising at least one selected from the group consisting of: the sgRNA molecule, the repair template, the isolated polynucleotides, the vector, and the host cell, and combinations thereof.

The invention also relates to a kit comprising at least one selected from the group consisting of: the sgRNA molecule, the repair template, the isolated polynucleotides, the vector, and the host cell, and combinations thereof.

The features, characteristics, advantages and embodiments specified herein with respect to the gene editing system according to the invention apply to the isolated polynucleotides, the vectors, the host cells, the pharmaceutical compositions, the kits, and the methods according to the invention in a corresponding manner, even if not specifically indicated.

It is to be understood that the before-mentioned features and those to be mentioned in the following cannot only be used in the combination indicated in the respective case, but also in other combinations or in an isolated manner without departing from the scope of the invention.

The invention is now further explained by means of embodiments resulting in additional features, characteristics and advantages of the invention. The embodiments are of pure illustrative nature and do not limit the scope or range of the invention. The features mentioned in the specific embodiments are general features of the invention which are not only applicable in the specific embodiment but also in an isolated manner and in the context of any embodiment of the invention.

The invention is now described and explained in further detail by referring to the following non-limiting examples and figures.

DESCRIPTION OF PREFERRED EMBODIMENTS

1. Methods

Ethical Clearance

Figure 1:
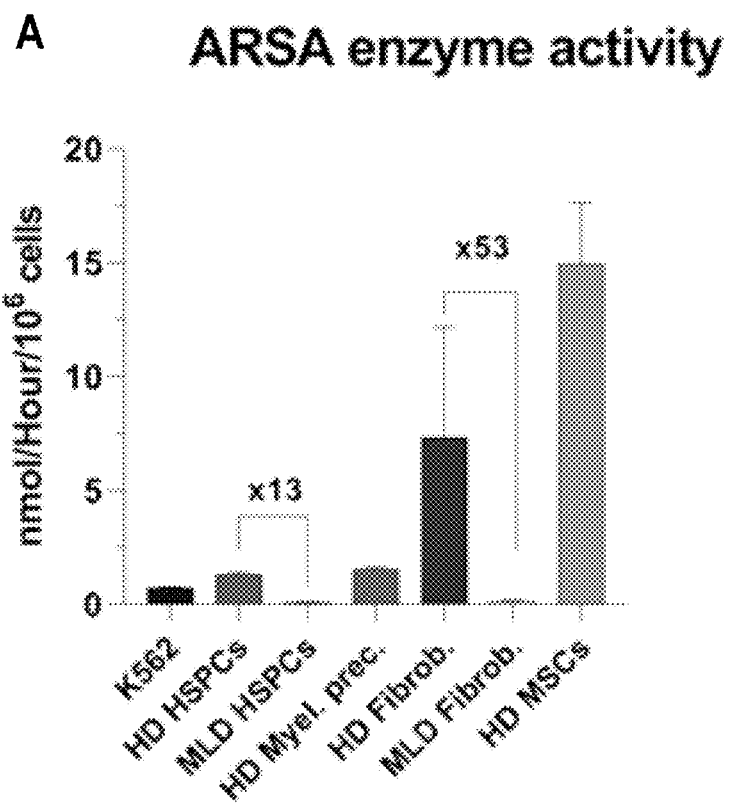
FIG. 1: (A) ARSA enzyme activity of cell pellets from hematopoietic stem and progenitor cell (HSPCs), myeloid derived-precursor cells, and fibroblasts of three healthy donors and three metachromatic leukodystrophy (MLD) patients. The cell numbers of $2\times10^5$ cells were used for measuring ARSA enzyme activity across different cell types. (B) Schematic representation of the ARSA gene locus and target sequences for each single-guide RNA (sgRNA), where protospacer adjacent motif sequences are highlighted in bold letters. (C) Cell-free in vitro screening of the five sgRNAs using ribonucleoprotein (RNP) complex on target polymerase chain reaction (PCR) amplicon with a size of 678 bp. The theoretical expected size post double-strand breaks for each sgRNA is: sgRNA1:387+291 bp; sgRNA2: 340+338 bp; sgRNA3:115+563 bp; sgRNA4:294+384 bp; sgRNA5:413+265 bp. (D) Screening of the five sgRNAs in healthy HSPCs derived from three different donors. Insertion and deletion (indel) percentages were determined by Inference of CRISPR Edits (ICE) analysis. (E) Guide-seq analysis to identify off-targets in HSPCs after transfection of sgRNA-5 and dsODN in combination with wild-type Cas9 or HiFi Cas9. Indels and dsODN integration using sgRNA-5. (F) Target sequences are shown at the top; matches are represented by dots, while mismatches are highlighted underneath (no mismatches found). GUIDE-seq reads are shown to the right of each on-target/off-target site.
Figure 1:
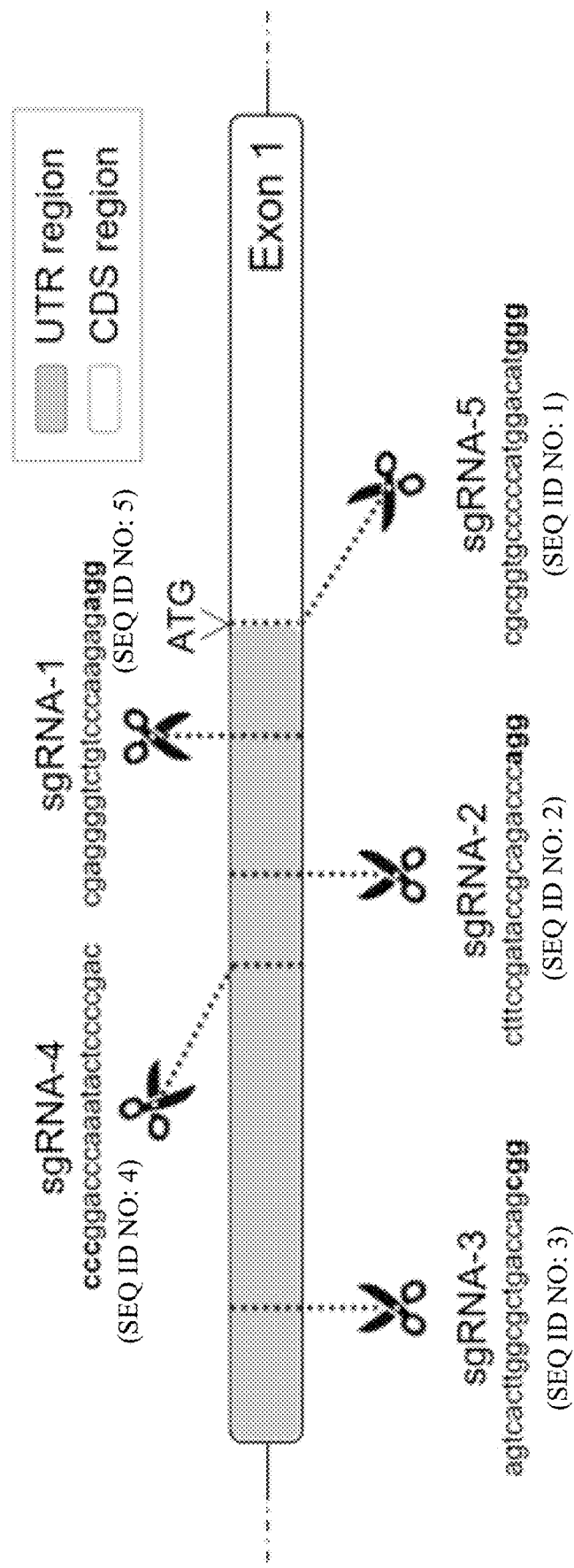
Figure 1:
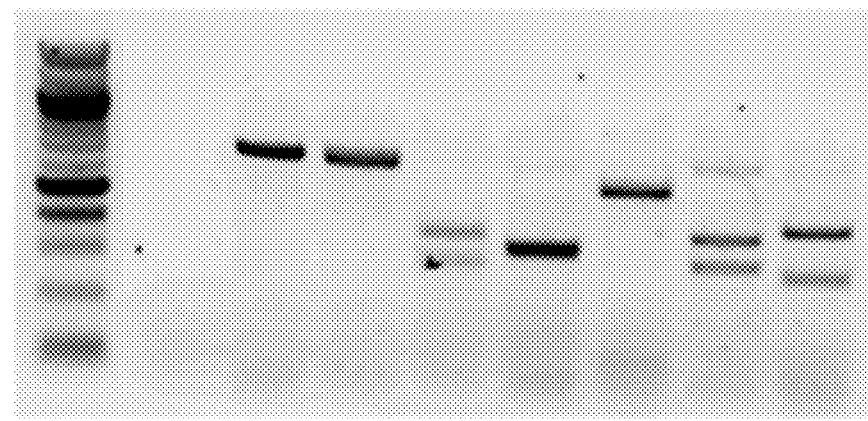
Figure 1:
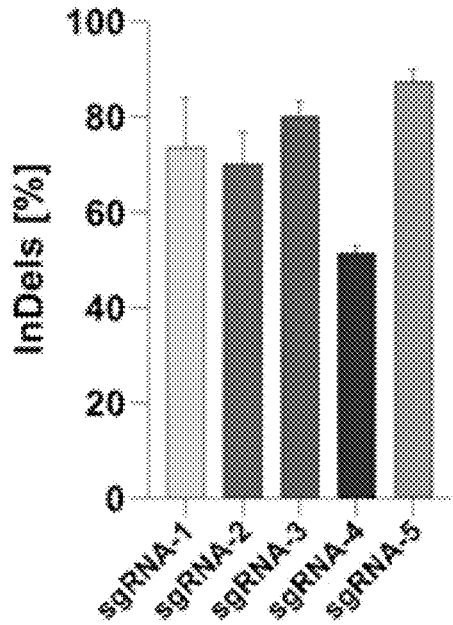
Figure 1:
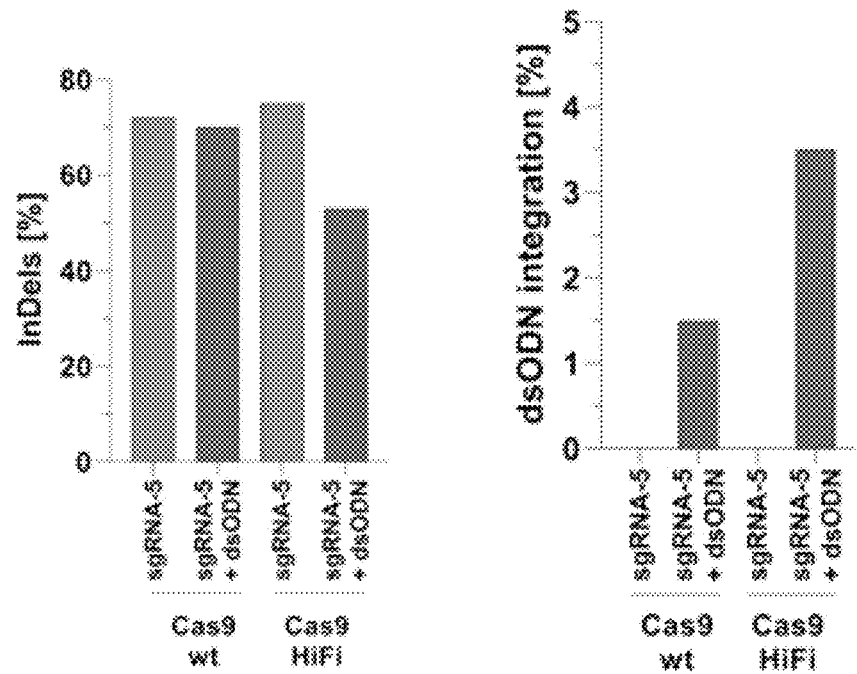
Figure 1:
Figure 1:

Human mobilized peripheral blood CD34$^+$ HSPCs from individual donors were obtained using protocols approved by the local ethics and after informed written consent (ethical approval number 088/2018BO1), as well as a leukapheresis from Key Biologics.

Isolation of CD34$^+$ HSPCs and in vitro myeloid differentiation CD34+HSPCs were enriched using a magnetic-activated cell sorting system (CliniMACS System; Miltenyi Biotec) according to the manufacturer's instructions. The purity of enriched HSPCs from both healthy donors and MLD patients was >90% for all isolated samples (data not shown). CD34$^+$ HSPCs were cultured according to the two-phase myeloid differentiation protocol reported earlier. CD34$^+$ HSPCs were initially cultured in Stem-MACS HSPCs Expansion Media (Miltenyi Biotec) supplemented with human stem-cell factor (SCF; 100 ng/ml) and interleukin-3 (100 ng/ml; Miltenyi Biotec) at 37° C. with 5% $CO_2$ for the first 3 days.

Later, a two-phase myeloid differentiation protocol was followed. In phase 1 (days 3-6), GM-CSF (50 ng/ml) and M-CSF (50 ng/ml; Miltenyi Biotec) were added additionally to the media. From days 6 to 9 (phase 2), only M-CSF (50 ng/mL) was added, and finally the maturation of myeloid cells was monitored by flow cytometry (BD FACSCalibur) using FITC-conjugated anti-CD33 (Miltenyi Biotec), PE-conjugated anti-CD14 (Miltenyi Biotec), PerCP-conjugated anti-CD45 (Miltenyi Biotec), APC-conjugated anti-CD11b (Miltenyi Biotec) and APC-conjugated anti-CD66b (Miltenyi Biotec) at day 10.

Cloning of Donor Template Constructs in Recombinant Adeno-Associated Virus 6

Donor template constructs of ARSA-eGFP and ARSA-cDNA were in vitro synthesized by GeneArt (Thermo Fisher Scientific). These donor templates were cloned into the pAAV.CMV.PI.EGFP.WPRE.bGH vector (Penn Vector Core) along with XhoI and NheI restriction sites. The vectors were amplified in DH5a competent cells (Sigma-Aldrich), isolated using standard plasmid isolation kits (VWR Peqlab) and verified by Sanger sequencing performed at Eurofins (see sequence details in Table 1).

TABLE 1

Sequences of ARSA-eGFP and codon-optimized ARSA-cDNA repair templates.
Left and right homology arms are marked in lower case bold, eGFP, SV40 poly-A signal
indicated in underlined and cDNA are indicated in capital letters without underline.

| Repair template | Sequence |
| --- | --- |
| ARSA-cGFP (SEQ ID NO: 7) | tggtcagcgccaagtgacttacgccccgaccctgagcccggaccgctaggcgaggag-gatcagatctccgctcgagaatctgaaggtgccctggtcctggaggagttccgtcccagcccgcggtctcccggtactgtcgggccccggccctctggagcttcaggaggcggccgtcagggtcggggagtattt-gggtccggggtctcagggaagggcggcgcctgggtctgcggtatcggaaagagcctgctggagccaagtagccctccctctcttgg gacagaccccctcggtaacatgGTGAGCAAGGGCGAGGAGCTGTTCACCGGGGTGGTGCCCATCCTGGTCGAGCTGGACGGCGACGT AAACGGCCACAAGTTCAGCGTGTCCGGCGAGGGCGAGGGCGATGCCACCTACGGCAAGCTGACCCTGAAGTTCATCTGCAC CACCGGCAAGCTGCCCGTGCCCTGGCCCACCCTCGTGACCACCCTGACCTACGGCGTGCAGTGCTTCAGCCGC TACCCCGACCACATGAAGCAGCACGACTTCTTCAAGTCCGCCATGCCCGAAGGCTACGTCCAGGAGCGCACC ATCTTCTTCAAGGACGACGGCAACTACAAGACCCGCGCCGAGGTGAAGTTCGAGGGCGACACCCTGGTGAAC CGCATCGAGCTGAAGGGCATCGACTTCAAGGAGGACGGCAACATCCTGGGGCACAAGCTGGAGTACAACTAC AACAGCCACAACGTCTATATCATGGCCGACAAGCAGAAGAACGGCATCAAGGTGAACTTCAAGATCCGCCAC AACATCGAGGACGGCAGCGTGCAGCTCGCCGACCACTACCAGCAGAACACCCCCATCGGCGACGGCCCCGTG CTGCTGCCCGACAACCACTACCTGAGCACCCAGTCCGCCCTGAGCAAAGACCCCAACGAGAAGCGCGATCAC ATGGTCCTGCTGGAGTTCGTGACCGCCGCCGGGATCACTCTCGGCATGGACGAGCTGTACAAGTAAACTTGT TTATTGCAGCTTATAATGGTTACAAATAAAGCAATAGCATCACAAATTTCACAAATAAAGCATTTTTTTCACTG CATTCTAGTTGTGGTTTGTCCAAACTCATCAATGTATCTTAtccatgggggcac-cgcggtccctcctcctggccctggctgctggcctggccgttgcccgtccgcccaacatcgtgctgatctttgccgacgacctcggc tatggggacctgggctgctatgggcaccccagctctaccactcccaacctggaccagctggcggcgg-gagggctgcggttcacagacttctacgtgcctgtgtctctgtgcacaccctctaggtaaagaggggccgcgcctcttcccgccc cgaccctccatccctttcctcccaatggattgcaggggggcgggaaaa |
| ARSA-cDNA (SEQ ID NO: 6) | tggtcagcgccaagtgacttacgccccgaccctgagcccggaccgctaggcgaggag-gatcagatctccgctcgagaatctgaaggtgccctggtcctggaggagttccgtcccagcccgcggtctcccggtactgtcgggccccggccctctggagcttcaggaggcggccgtcagggtcggggagtattt-gggtccggggtctcagggaagggcggcgcctgggtctgcggtatcggaaagagcctgctggagccaagtagccctccctctcttgg gacagaccccctcggtaacatgAGCATGGGAGCCCCTAGATCTCTGCTGCTGGCTCTGGCTCTGGACTGGCAGTTGCCAGACCTCC TAACATCGTGCTGATCTTCGCCGACGATCTCGGCTATGGCGATCTGGGCTGTTACGGACACCCCAGCAGCACCACACCTAACC TGGATCAACTTGCCGCTGGCGGCCTGAGATTCACCGATTTCTACGTGCCCGTGTCTCTGTGCACCCCTTCTAGA GCTGCTCTGCTGACAGGCAGACTCCCTGTGCGGATGGGAATGTATCCTGGCGTGCTGGTGCCTTCCAGTAGAG GCGGACTGCCTCTGGAAGAAGTGACAGTTGCCGAAGTGCTGGCCGCCAGAGGATATCTGACTGGCATGGCCG GAAAGTGGCACCTCGGAGTTGGACCTGAAGGCGCTTTTCTGCCTCCTCACCAGGGCTTCCACCGGTTTCTGGG CATCCCTTACTCTCACGATCAGGGCCCCTGCCAGAACCTGACCTGTTTTCCTCCTGCCACACCTTGCGACGGCG GCTGTGATCAAGGACTGGTGCCTATTCCTCTGCTGGCCAACCTGAGCGTGGAAGCTCAACCTCCTTGGCTGCC AGGACTGGAAGCCCGGTATATGGCCTTCGCTCACGACCTGATGGCCGACGCTCAGAGACAGGACAGACCATT CTTCCTGTACTACGCCAGCCACCACACACACTACCCTCAGTTTAGCGGCCAGAGCTTCGCCGAGAGATCTGGC AGAGGACCTTTCGGCGACAGCCTGATGGAACTGGATGCCGCTGTGGGCACACTGATGACAGCAATTGGAGAT CTGGGACTGCTGGAAGAGACACTGGTCATCTTCACCGCCGACAACGGCCCCGAGACAATGAGAATGTCTAGA GGCGGCTGTAGCGGCCTGCTGAGATGTGGCAAGGGCACCACATATGAAGGCGGCGTCAGAGAACCTGCTCTG GCCTTTTGGCCTGGCCATATTGCTCCAGGCGTGACACACGAGCTGGCCTCTTCTCTGGACTTCTGCTGCCTACACT GGCAGTCTTGCTGGTGCTCCCCTGCCTAATGTGACCCTGGATGGCTTCGATCTGAGCCCACTGCTGCTCGGCA CAGGCAAGTCTCCAAGACAGAGCCTGTTCTTCTACCCTAGCTACCCCGATGAAGTGCGGGGAGTGTTTGCCGT GCGGACCGGAAAGTATAAGGCCCACTTCTTCACCCAAGGCAGCGCCCACTCTGACACCACAGCTGATCCTGCT TGTCACGCCAGCTCTAGCCTGACAGCCCATGAACCTCCACTGCTGTACGACCTGAGCAAGGACCCCGGCGAGA ACTACAATCTGCTTGGCGGAGTTGCCGGCGCTACACCTGAAGTTCTGCAGGCCCTGAAACAGCTCCAGCTGCT GAAAGCCCAGCTGGACGCTGCCGTGACATTTGGACCTAGTCAGGTGGCCAGAGGCGAGGATCCTGCTCTGCA GATCTGTTGTCACCCTGGCTGCACACCCAGACCTGCCTGCTGTCATTGTCCTGATCCTCACGCCTGAAACTTGT TTATTGCAGCTTATAATGGTTACAAATAAAGCAATAGCATCACAAATTTCACAAATAAAGCATTTTTTTCACTG CATTCTAGTTGTGGTTTGTCCAAACTCATCAATGTATCTTAtccatgggggcac-cgcggtccctcctcctggccctggctgctggcctggccgttgcccgtccgcccaacatcgtgctgatctttgccgacgacctcggc tatggggacctgggctgctatgggcaccgcggtccctcctcctggccctggctgctggcctggccgttgcccgtccgcccaacatc gtgctgatctttgccgacgacctcggctatggggacctgggctgctatgggcaccccagctctaccactcccaacctggaccagct ggcggcgg-gagggctgcggttcacagacttctacgtgcctgtgtctctgtgcacaccctctaggtaaagaggggccgcgcctct tccccgccccgaccctccatccctttcctcccaatggattgcaggggggcgggaaaa |

Production, Concentration, and Titration of Adeno-Associated Virus 6

Lenti-X 293T cells (5×10⁶) were seeded in a T175 culture flask (Corning) without antibiotics. After 48 h, Dulbecco's modified Eagle's medium (DMEM; Biochrom) was replaced by 9 mL Opti-MEM (Thermo Fisher Scientific), and the cells were transfected using each 32 μg of JetPEI complexed (Polyplus transfection) adeno-associated virus (AAV) vector: pAAV2.6 (Penn Vector Core), pAdDeltaF6 (Penn Vector Core), and ARSA-eGFP/ARSA-cDNA transfer plasmid. Six hours after transfection, cells were washed and subsequently cultured in 10 mL DMEM supplemented with 10% fetal bovine serum (Gibco) and 1% L-Glu (Biochrom).

The viral supernatant was harvested 72 h post transfection and concentrated by ultracentrifugation at 4° C. for 4 h at 280,000 g. Virus pellets were re-suspended in 100 μL StemMACS medium and stored at −80° C. Virus titers were determined by quantitative polymerase chain reaction (qPCR) and droplet digital PCR (ddPCR). To obtain viral DNA from disrupted AAV capsids, 2 μL concentrated virus supernatant was digested with 2 IU of DNase I (NEB) at a final volume of 40 μL. Samples were incubated at 37° C. for 30 min and at 75° C. for 15 min. Proteinase K (1 μL; Qiagen) was added to 5 μL of the DNase I digested product at a final volume of 20 μL and incubated at 50° C. and 98° C. for 30 and 10 min, respectively.

A qPCR was run with 2 μL proteinase K digested product, 12.5 μL KAPA Probe FAST (Bio-Rad), 1 μL each ITR primer (5 μM) and ITR probe (5 μM), and 2.5 μL of H₂O in CFX Real-Time PCR cycler (Bio-Rad) for 3 min at 95° C., and 40 cycles of 3 s at 95° C. and 20 s at 60° C. Alongside, the ddPCR was run on the C1000 Touch Thermal Cycler (Bio-Rad): 10 min at 95° C., 40 cycles of 30 s at 95° C., 1 min at 57°C, and 2 min at 72° C., followed by enzyme inactivation at 98° C. for 10 min. Primers and probes are listed in Table 2.

TABLE 2 sgRNA target sequences and off-target in silico predictions utilizing the online tool CHOPCHOP; the protospacer adjacent motif sequence is underlined, sgRNA = single-guide RNA

| Target | sgRNA sequence | Target sequence (5'-3') | Off-targets in silico |
|---|---|---|---|
| sgRNA-1 | cgaggggtctgtcccaagagagg (SEQ ID NO: 5) | CTCTTGGGACAGACCCCTCG (SEQ ID NO: 8) | 6 |
| sgRNA-2 | ctttccgataccgcagacccagg (SEQ ID NO: 2) | GGGTCTGCGGTATCGGAAAG (SEQ ID NO: 9) | 3 |
| sgRNA-3 | agtcacttggcgctgaccagcgg (SEQ ID NO: 3) | CTGGTCAGCGCCAAGTGACT (SEQ ID NO: 10) | 10 |
| sgRNA-4 | cccggacccaaatactcccc gac (SEQ ID NO: 4) | GTCGGGGAGTATTTGGGTCC (SEQ ID NO: 11) | 6 |
| sgRNA-5 | cgcggtgcccccatggacatggg (SEQ ID NO: 1) | ATGTCCATGGGGGCACCGCG (SEQ ID NO: 12) | 1 |

In Vitro CRISPR-Cas9 Cutting Assay

The cutting potential of the synthesized single-guide RNAs (sgRNAs; IDT) were validated via the in vitro cleavage assay according to the protocol from IDT. In brief, the target DNA sequence was amplified, and 100 ng PCR product was incubated with the ribonucleoprotein (RNP) complex (sgRNA:RNP) for 2 h at 37° C. The reaction was stopped by adding proteinase K for 10 min at 56° C. The resulting products were visualized on a 1% agarose gel.

Gene Editing of Human CD34+ HSPCs

Forty-eight hours prior to electroporation, CD34+ HSPCs were thawed in StemMACS HSPCs Expansion Media supplemented with 100 ng/μL SCF, 20 ng/μL TPO, and 100 ng/μL Ftl-3 (Miltenyi Biotec). RNP complex was formed by mixing Cas9 protein (IDT) and sgRNAs at a molar ratio of 1:2 (45 and 90 μmol) at room temperature for 15 min. Following the formation of the complex, 1×10$^5$ CD34+ HSPCs were transfected using a 10 μL Neon transfection kit (Thermo Fisher Scientific) with the following settings: 1,650 V, 10 ms, three pulses. Then, they were transferred to myeloid differentiation media. Fifteen minutes post transfection, HSPCs were transduced with ARSA-eGFP-AAV and ARSA-cDNA-AAV at a multiplicity of infection (MOI) of 2,000, 1,000, and 500, respectively.

Gene Editing Analysis

Edited CD34+ HSPCs were further differentiated to myeloid lineage for up to 10 days. On day 5, aliquots were collected for DNA isolation, Sanger sequencing, and Inference of CRISPR Edits (ICE) analysis. On day 10, cells were harvested for RNA isolation, quantitative reverse transcription PCR (qRT-PCR), myeloid differentiation analysis, cell proliferation analysis, and quantitative arylsulfatase-A functional assays. Finally, HDR rates were quantified by flow cytometry uniquely for ARSA-eGFP and by multiplex in-out ddPCR for both ARSA-eGFP and ARSA-cDNA using the primers and probes indicated in Table 3. β2-microglobulin (β2M) was used as a reference gene in ddPCRs.

ICE Analysis

Five days post transfection, genomic DNA was isolated using a NucleoSpin Tissue Kit following the manufacturer's protocol (Machery-Nagel). The target regions were amplified and purified using GoTaq Colorless Master Mix (Promega) and a QIAquick PCR Purification Kit (Qiagen), respectively. Primers for each target are listed in Table 3. Following the sequencing of the purified products by Sanger sequencing, the insertion and deletion (indel) rate was analyzed with the help of web the tool ICE.

RNA Isolation, cDNA Synthesis, and qRT-PCR Assays

Total RNA was isolated using a RNeasy Mini Kit (Qiagen) on day 10 post transfection, followed by cDNA synthesis using a QuantiTect Reverse Transcription Kit (Qiagen). cDNA was amplified and quantified using the CFX96 TM Real-Time PCR Detection System (Bio-Rad) with KAPA SYBR FAST 2×MasterMix (KAPA Biosystems). Primer sequences are shown in Table 3. Results were normalized against the expression of β2M. The crossing point (CP) values for the unknown samples were evaluated with the formula 2 (CP β2M-CP target gene).

The qRT-PCR primers are designed to detect codon-optimized ARSA transcripts (transgene-specific) and do not detect endogenous ARSA expression and vice versa. For samples without transgene transduction (i.e., control, sgRNA-5-only treated sample), no signal was noticed in qPCR analysis, and we set the Ct values to the maximum number of cycles (in our case 40) to calculate fold changes. Several software tools (e.g., Applied Biosystems DataAssist v3.0 and Integromics RealTime StatMiner) utilize a similar approach by setting undetermined values to a maximum Ct value. Therefore, the actual fold changes are biased (in other words, overestimated), but this allows plotting of relative expression values for codon-optimized mRNA in CRISPR+AAV-treated samples in comparison to the controls.

ddPCR

Mastermix for PCR was prepared by adding the following components to a final volume of 20 μL: ddPCR Multiplex Supermix (Bio-Rad), primers (950 nM), probes (250 nM), and DNA (350 ng). Using a QX200 ddPCR droplet generator (Bio-Rad), DNA was separated into approximately 20,000 droplets, transferred to a 96-well plate, and sealed to avoid evaporation using the PX1 PCR Plate Sealer (Bio-Rad). PCR was run on the C1000 Touch Thermal Cycler (Bio-Rad) for 10 min at 95° C. in 40 cycles comprising 30 s at 95° C., 1 min at 61° C., and 2 min at 72° C. followed by enzyme inactivation at 98°C for 10 min. Finally, PCR products were examined by the QX2000 droplet reader (Bio-Rad) and analyzed with QuantaSoft v1.6.6 (Bio-Rad).

Quantitative Arylsulfatase: A Functional Assay

The enzyme activity of arylsulfatase-A was measured using the artificial substrate p-nitrocatecholsulfate (pNCS;

Merck) as described in the art. In brief, the cell lysate ($2.5 \times 10^6$/mL) was incubated with substrate solution (10 mM pNCS, 0.5 mM sodium pyrophosphate, 10% sodium chloride in 0.5 M sodium acetate buffer, pH 5.0) for 48 h at 8°C. Finally, substrate turnover was measured photometrically at 514 nm after adding 0.5 M NaOH.

Off-Target Analysis Using GUIDE-Seq

The utilized oligos and dsODNs sequence was derived from the original GUIDE-seq report and synthesized at Metabion. CD34+ cells were transfected with dsODN at an optimal concentration (5, 15, and 25 μmol) together with the sgRNAs and Cas9 RNP at a molar ratio of 2:1. DNA was isolated using a DNeasy Blood and Tissue Kit (Qiagen) after 5 days. DNA fragments of 200-450 bp were generated and ligated to adaptors with a NEBNext Ultra II Kit (NEB). The first DNA amplification employed NEBNext Ultra II Q5 Master Mix (NEB), and KAPA SYBR FAST 2×MasterMix (KAPA Biosystems) was used for the second amplification. Later, libraries were pooled and loaded into three lanes of an Illumina GAIIx single-read flow cell and two MiSeq flow cells.

Bound molecules were clonally amplified on a cBot instrument. Subsequently, the first 50 nt from each fragment were sequenced followed by a 7-nt sequencing run to decipher the barcode sequence in the adapter (Illumina). The Guide-seq Analysis package v1.0.2 within a singularity container was used first to demultiplex and then to consolidate duplicate PCR reads of the raw sequence data using the GRch37.75 human genome primary assembly as reference. This was followed by cleavage site recognition, off-target activity identification, and visualization. The read alignment step of the pipeline was conducted using BWA-mem v0.7.9a-r786, and BEDTools v2.25.0 was used for downstream analysis.

Statistics

Student's t-test was used to determine significant differences between mean values using GraphPad Prism v8.1.0 (GraphPad Software, San Diego, CA).

2. Results

ARSA expression in CD34+ HSPCs First, the inventors aimed to assess ARSA enzyme activity across different cell types to choose the most accurate model. For this purpose, the inventors conducted an ARSA enzyme activity assay utilizing various cell types comprising HSPCs, myeloid precursors (healthy HSPCs differentiated to myeloid lineage), fibroblasts, and mesenchymal stromal cells (MSCs), which were obtained from either healthy donors or MLD patients (late-infantile phenotype with heterozygous mutation [P426L/P180R]), respectively.

The data showed that HSPCs expressed functional ARSA enzymes but at a lower level in comparison to fibroblasts and MSCs (FIG. 1, A). As expected, fibroblasts from MLD patients showed ~53-fold decreased ARSA activity in comparison to healthy fibroblasts ($0.137 \pm 0.076$ nmol/h/$10^6$ cells vs. $7.32 \pm 8.39$ nmol/h/$10^6$ cells, respectively), while HSPCs from MLD patients ($0.097 \pm 0.01$ nmol/h/$10^6$ cells) had ~13-fold decreased activity compared to healthy HSPCs ($1.3 + 0.28$ nmol/h/$10^6$ cells).

Design and Efficacy Assessment of sgRNAs Targeting ARSA Gene

To accomplish mutation-agnostic correction for MLD, the inventors targeted the endogenous ARSA locus in closer proximity to the transcription start site and designed more than 50 different sgRNAs using different online tools (CHOP-CHOP, Synthego, etc.) or manual design based on the NGG proto-spacer adjacent motif sequence in both strands. Next, the inventors performed a score-matrix analysis in which weight was given to recurrent hits in different tools, closer proximity to the first codon (ATG), non-disturbance of transcription factor binding sites in 5' UTR, and fidelity of sgRNA with fewer than 10 in silico predicted off-targets.

Following these premises, the inventors ultimately selected five different sgRNAs within their target region of ARSA 5' UTR or in closer proximity to the transcription start site (FIG. 1, B), and all sgRNAs showed 10 or fewer in silico predicted off-targets (Table 2). As a first experiment, the inventors validated their sgRNAs for the on-target cleavage potential in a cell-free in vitro CRISPR-Cas9 cutting assay where the PCR product was incubated with the respective sgRNA:Cas9 RNP complex and the potential double-strand breaks (DSBs) were analyzed in an agarose gel after 2 h of incubation. The obtained results revealed that all sgRNAs showed a high level of on-target gene editing (range 88-97%; FIG. 1, C). Next, the inventors aimed to validate their selected gRNA experimentally in HSPCs derived from a healthy donor. The inventors electroporated HSPCs with RNP which was formed by Cas9 and the respective sgRNA at a molar ratio of 1:2, and the inventors measured the targeted gene editing with ICE analysis using Sanger sequence electropherograms derived from edited and unedited cells. The results revealed that the indel frequencies in HSPCs were sgRNA dependent, and sgRNA-5 led to the highest indel score (87%; FIG. 1, D). Based on the experimental evidence and reduced in silico predicted off-target score (only one off-target; Table 2), the inventors selected sgRNA-5 as the lead sgRNA for further experiments. The inventors next sought to determine the specificity profile of sgRNA-5 using GUIDE-seq analysis, which identifies unbiased genome-wide off-targets.

TABLE 3

Oligonucleotide sequences utilized for PCR, qRT-PCR, and ddPCR; PCR = polymerase chain reaction, qPCR = quantiative PCR, ddPCR = droplet digital PCR, ICE = Inference of CRISPR Edits.

| Target | qPCR/ddPCR | Primer | Primer sequence | SEQ ID NO: |
|---|---|---|---|---|
| AAV titration (ITR) | qPCR | For | GGAACCCCTAGTGATGGAGTT | 13 |
| | | Rev | CGGCCTCAGTGAGCGA | 14 |
| | | FAM-Probe | CACTCCCTCTCTGCGCGCTCG | 15 |
| ARSA (ICE analysis) | PCR | For | CGCAAGGGTCACAGGTCACG | 16 |
| | | Rev | AGGAAAGGGATGGAGGGTCG | 17 |
| ARSA wild-type cDNA | qPCR | For | TCTACCCGTCCTACCCAGAC | 18 |
| | | Rev | CAGAGCCCTGGGTGAAGAAG | 19 |

TABLE 3-continued

Oligonucleotide sequences utilized for PCR, qRT-PCR, and ddPCR; PCR = polymerase chain reaction, qPCR = quantiative PCR, ddPCR = droplet digital PCR, ICE = Inference of CRISPR Edits.

| Target | qPCR/ddPCR | Primer | Primer sequence | SEQ ID NO: |
|---|---|---|---|---|
| | | FAM-Probe | GCTGTGCGGACTGGAAAGTA | 20 |
| ARSA codon-optimized cDNA | qPCR | For | GCACAGGCAAGTCTCCAAGA | 21 |
| | | Rev | TATACTTTCCGGTCCGCACG | 22 |
| | | FAM-Probe | ATGAAGTGCGGGGAGTGTTT | 23 |
| B2M | qPCR | For | ATCCAGCGTACTCCAAAGATTC | 24 |
| | | Rev | TGAAACCCAGACACATAGC | 25 |
| | | HEX-Probe | AGAATGGAAAGTCAAATTTCCT | 26 |
| | ddPCR | For | TGGCTGTGATACAAAGCGGT | 27 |
| | | Rev | GGAAACAACCAGGCAAAGAG | 28 |
| | | HEX-Probe | GATGAAGAAACTAAGGCACCG | 29 |
| eGFP/ARSA template | ddPCR | For | CACTGCATTCTAGTTGTGGT | 30 |
| | | Rev | GGTACATGCCCATCCGAAC | 31 |
| | | FAM-Probe | GTCCAAACTCATCAATGTATC | 32 |

Due to the inherent cell toxicity of dsODN in HSPCs, the inventors optimized the conditions to perform the GUIDE-seq directly on HSPCs safely, as the detection of off-targets is for clinical development. A dose escalation study with three different tested concentrations (25, 15, and 5 μmol) of dsODNs was studied, and the inventors found a dose of 15 pmol was well tolerated by HSPCs and resulted in 1.5% and 3.5% of on-target site integration after cutting with wild-type Cas9 and Hifi Cas9, respectively (FIG. 1, E).

This 15 pmol dose was employed in the GUIDE-seq experiment in combination with sgRNA-5 and either wild-type or HiFi Cas9. Five days after transfection, DNA was isolated to be employed for next-generation sequencing (NGS) library preparation and subsequent sequencing by the Illumina Miseq platform. The off-target profile of sgRNA-5 showed no detectable off-targets for either wild-type or HiFi Cas9 (FIG. 1F). Moreover, the number of reads was aligned with the percent of dsODN integration.

Mutation-Independent Gene Addition Approach for the Treatment of MLD

In the next step, the inventors explored the potential of sgRNA-5 in targeted gene integration. Focusing on its sequence, the inventors designed different repair templates with optimized codons for efficient translation of the transgene, a SV40 poly-A tail sequence (122 bp) after the transgene sequence to prevent the transcription of the mutated gene, and 300 bp homology arms to enhance the HDR pathway. The first repair template consisted of eGFP transgene, which was designed for absolute quantification of HDR in FACS analysis, and the second repair template comprised a mutation-free ARSA cDNA (for detailed DNA sequences, see Table 1). Both repair templates were cloned into AAV6 vectors without selectable markers and confirmed by Sanger sequencing (FIG. 2A).

Virus titers were calculated by ddPCR using the primers listed in Table 2, obtaining mean values of $3.4 \times 10^{11}$ and $9.4 \times 10^{10}$ TU/mL, respectively (data not shown). Next, AAV6 donor templates (both eGFP and ARSA cDNA) were employed at different MOI (2,000, 1,000, and 500) to transduce healthy donor-derived HSPCs cultured in myeloid differentiation medium immediately after gene editing. Ten days after gene editing and AAV transduction, cells were harvested and evaluated for gene correction score using different molecular analyses, including ddPCR, RT-PCR, and ARSA enzyme activity. In addition, the transduced cells with eGFP donor templates were measured in flow cytometry analysis.

Figure 2:
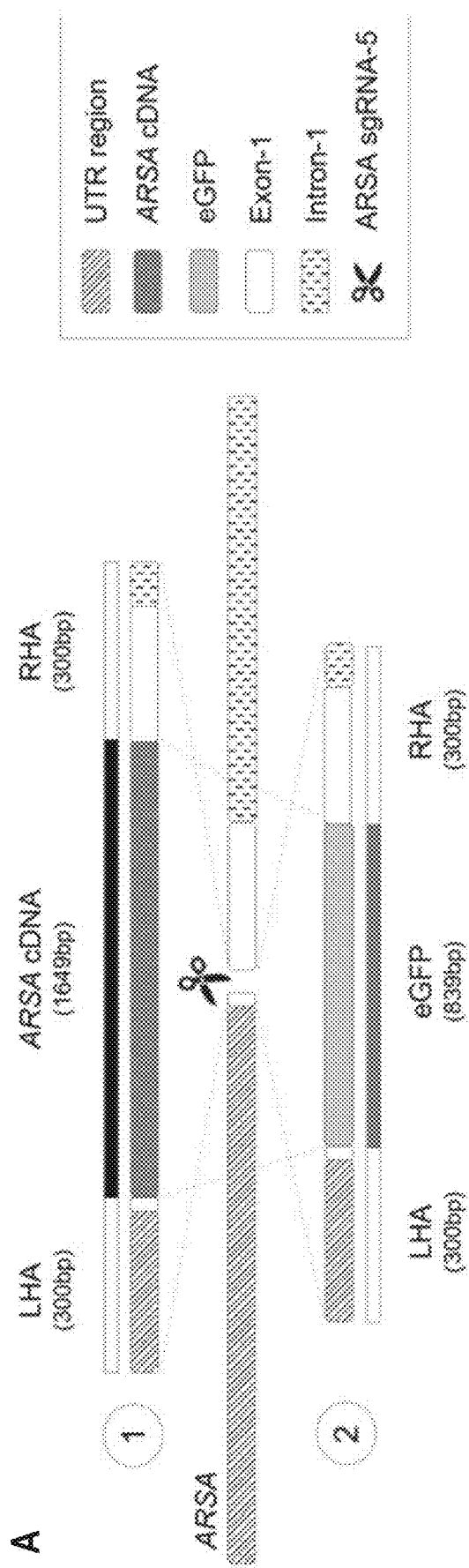
FIG. 2: Gene addition approach in healthy CD34$^+$ HSPCs. (A) Illustration of gene addition approaches comprising two different repair templates that encode for either eGFP or the codon-optimized ARSA cDNA. (B)-(E) HDR efficiencies attained with ARSA sgRNA-5 and AAV6-eGFP template at different multiplicity of infection (MOI; 2,000, 1,000, and 500) measured by flow cytometry ((B) and (C)) and droplet digital PCR (ddPCR) ((D) and (E)) on day 10. sgRNA-5, adeno-associated virus (AAV), and AAV+CRISPR treatments represent gene-edited samples, AAV-transduced samples, and AAV-transduced-CRISPR-edited samples, respectively. (F) Percentage of gene addition measured by ddPCR for sgRNA-5 in combination with AAV6 ARSA cDNA at the indicated MOI. (G) Specific detection of codon-optimized ARSA mRNA by quantitative reverse transcription PCR (qRT-PCR) after isolation of total RNA from edited myeloid-derived suppressor cells. (H) ARSA activity of wild-type, gene disrupted, AAV, and AAV+CRISPR-treated samples. (I) Flow cytometry analysis for CD33, CD11b, and CD66b on myeloid cells at day 10. All experiments were performed in triplicate with three different donors.
Figure 2:
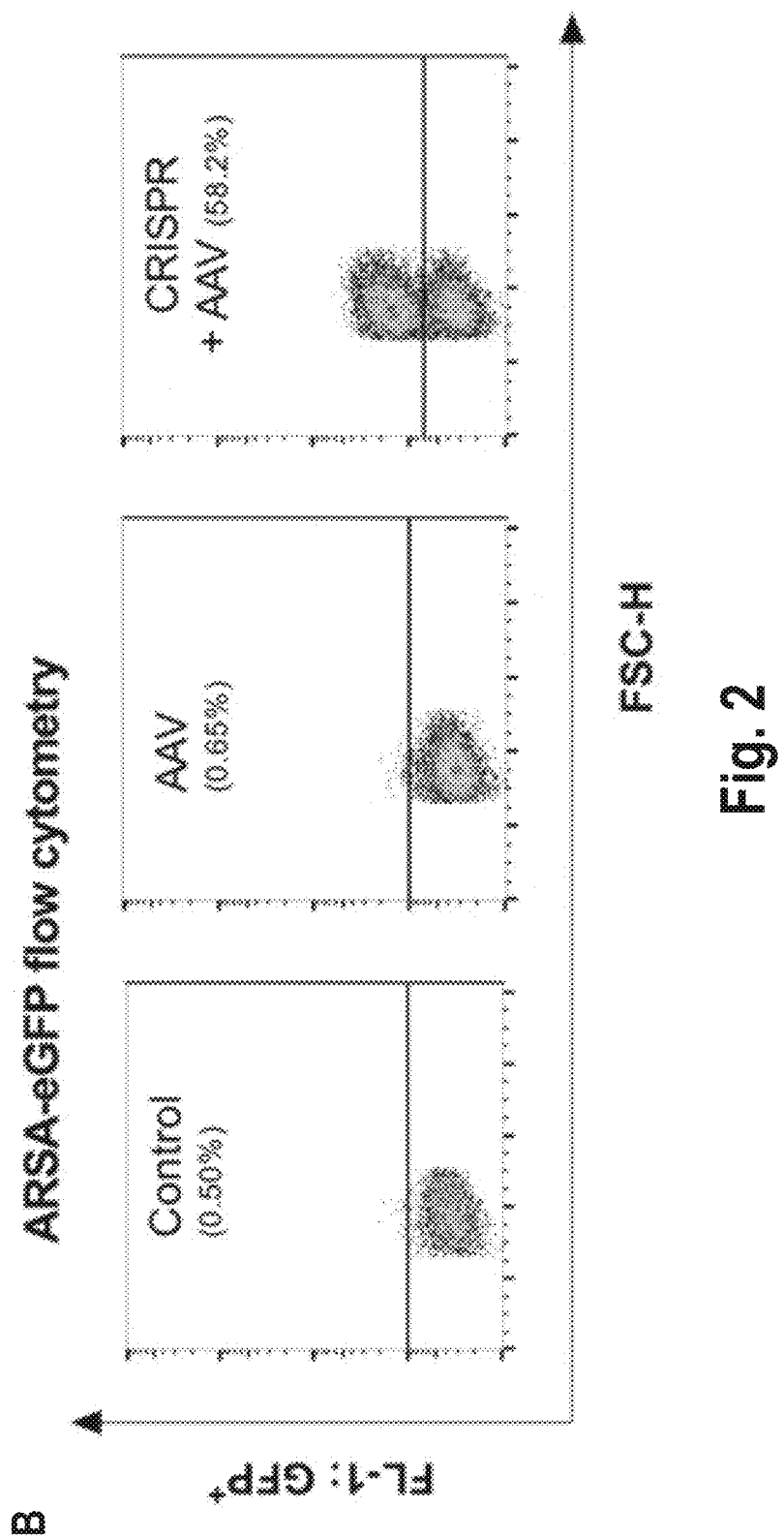
Figure 2:
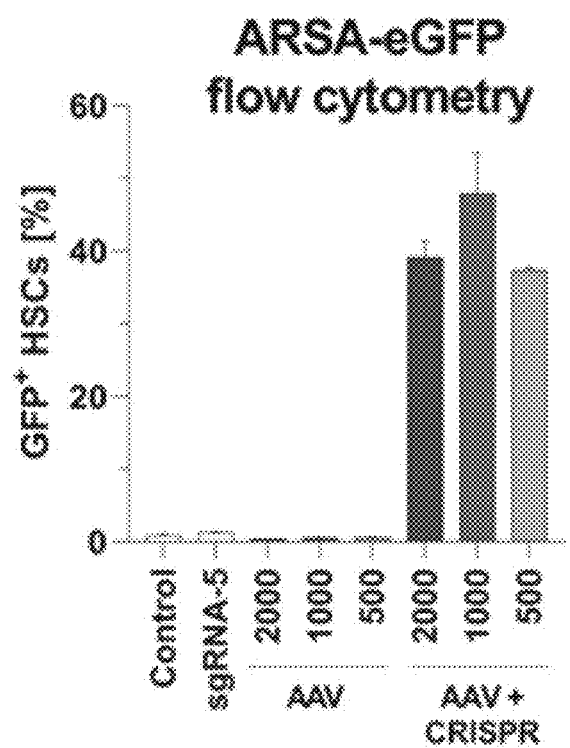
Figure 2:
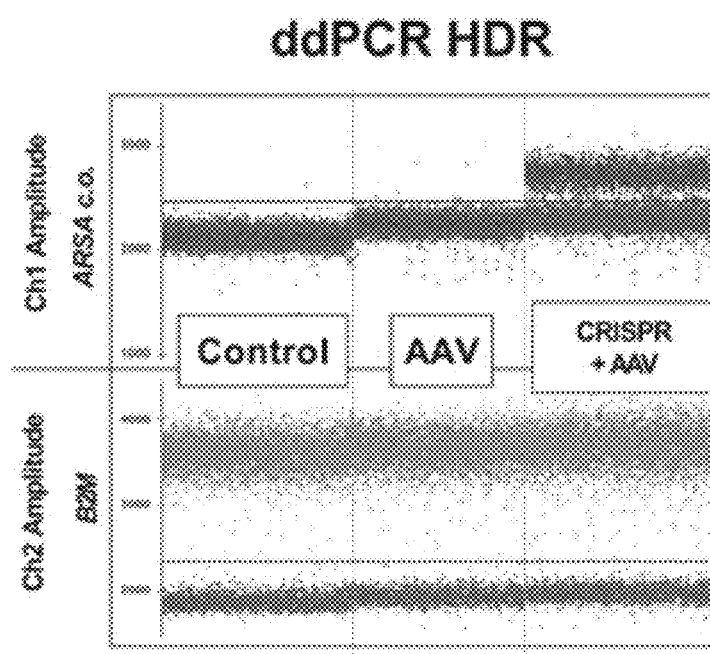
Figure 2:
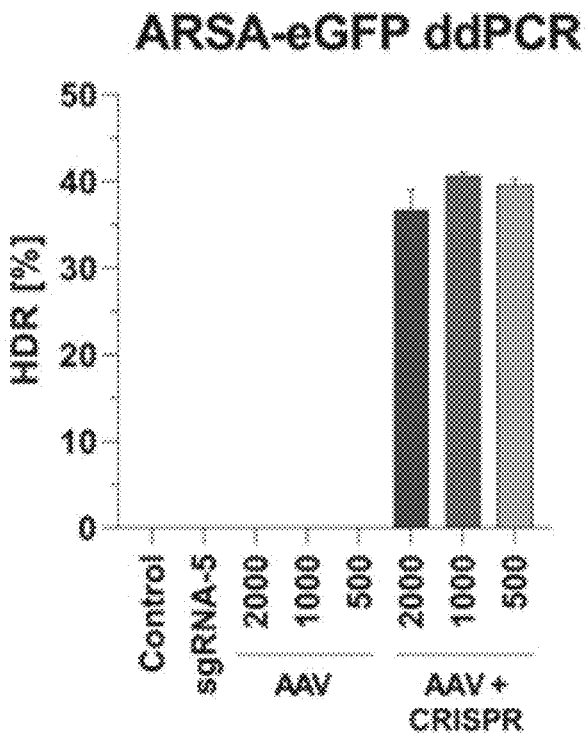
Figure 2:
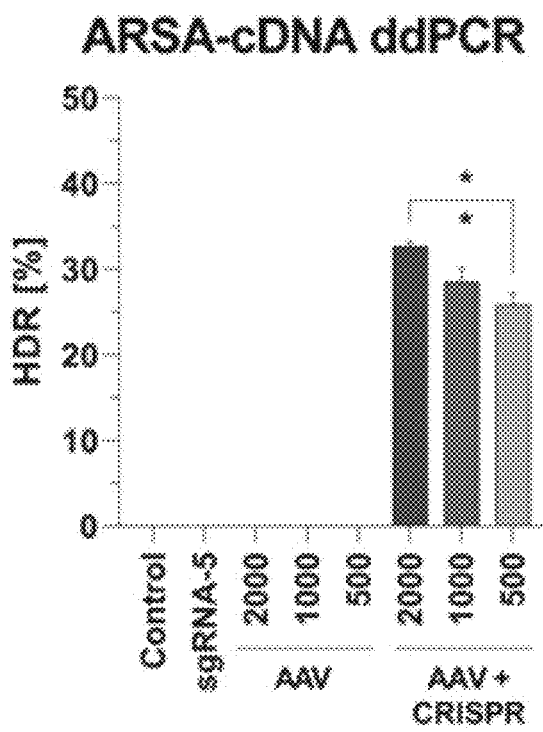
Figure 2:
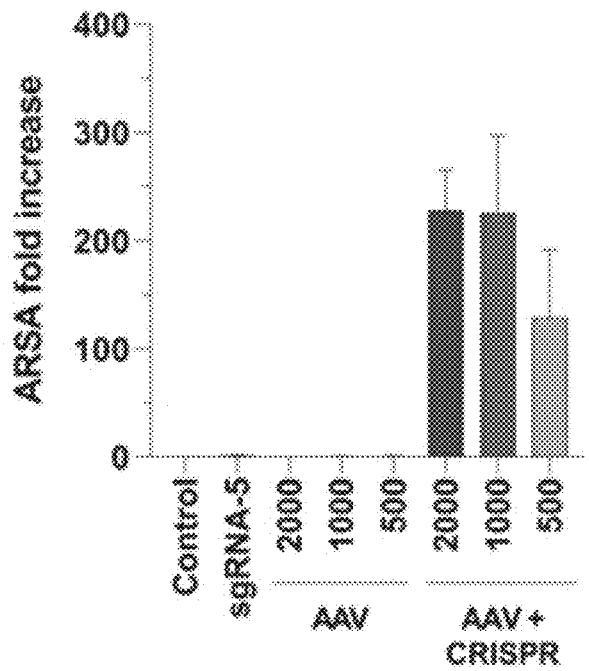
Figure 2:
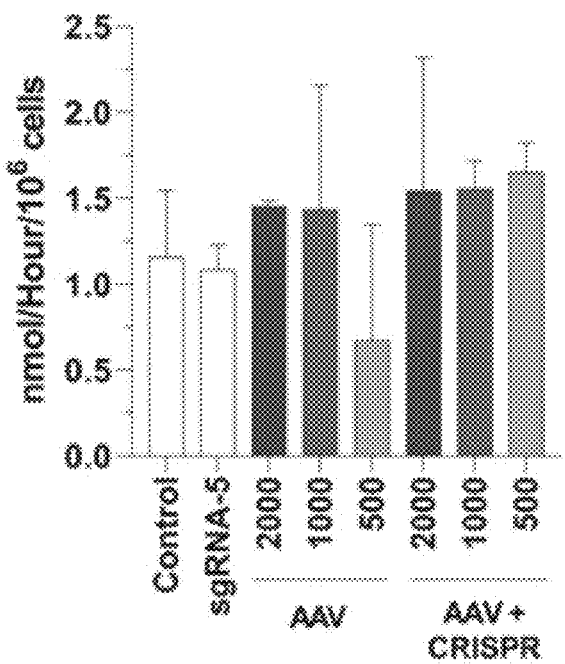
Figure 2:
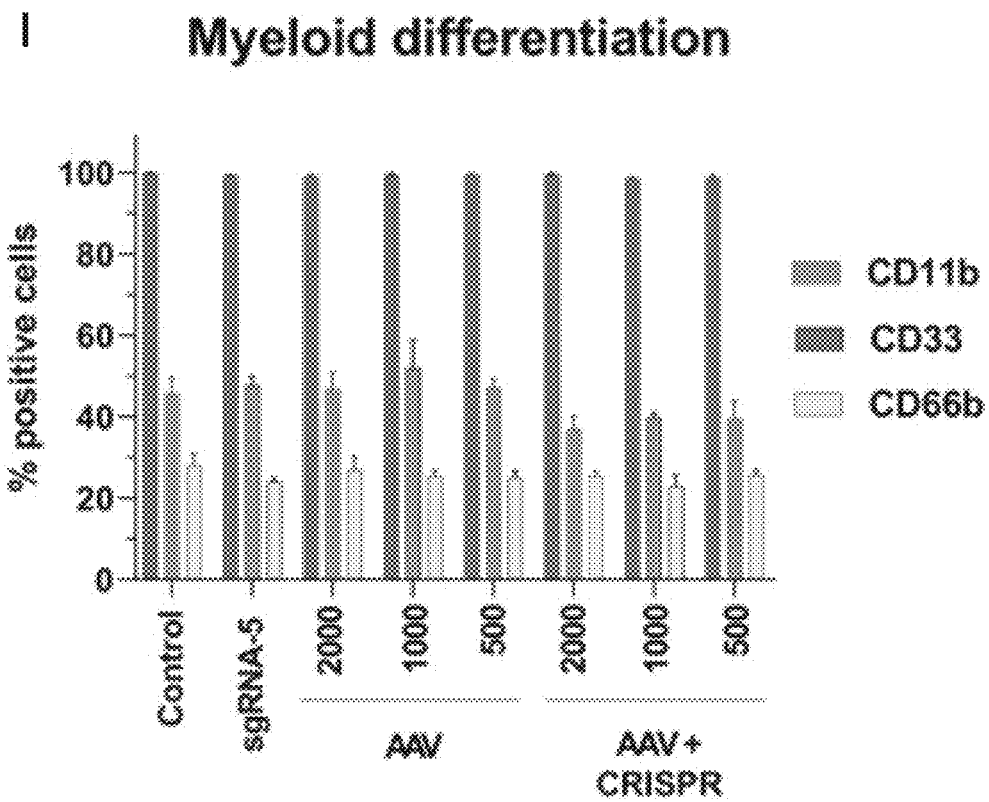

It should be noted that eGFP expression is only induced after successful integration in the endogenous ARSA locus under the control of an endogenous ARSA promotor. Strikingly, the results showed that the inventors' strategy was able to integrate eGFP in >47% of the transduced cells at a MOI of 1,000 (FIGS. 2, B and C). The other tested MOIs (500 and 2,000) provided 37% and 39% of eGFP transgene integration, respectively. An analysis with ddPCR in the same samples corroborated the obtained FACS results: samples electroporated with RNP (Cas9/sgRNA-5) along with transduction of AAV6-eGFP (MOI 1,000) displayed 40.6% transgene integration. Untreated samples or only AAV-treated samples did not provide a positive signal (FIGS. 2, D and E).

In the case of ARSA cDNA AAV6-transduced cells, a MOI of 2000 showed the best integration efficiency (32.7%; FIG. 2, F), whereas a MOI of 500 exhibited significantly reduced integration (25.8%; p<0.01). To assess the endogenous transcription of the integrated ARSA cDNA, the inventors designed qPCR primers and probes that exclusively bind with codon-optimized ARSA mRNA but not with the endogenous wild-type ARSA mRNA. In this qPCR experiment, we observed more than 220-fold increased expression of ARSA mRNA in AAV+CRISPR-treated samples compared to cells treated only with AAV or untreated samples derived from healthy donors (FIG. 2, G).

Figure 3:
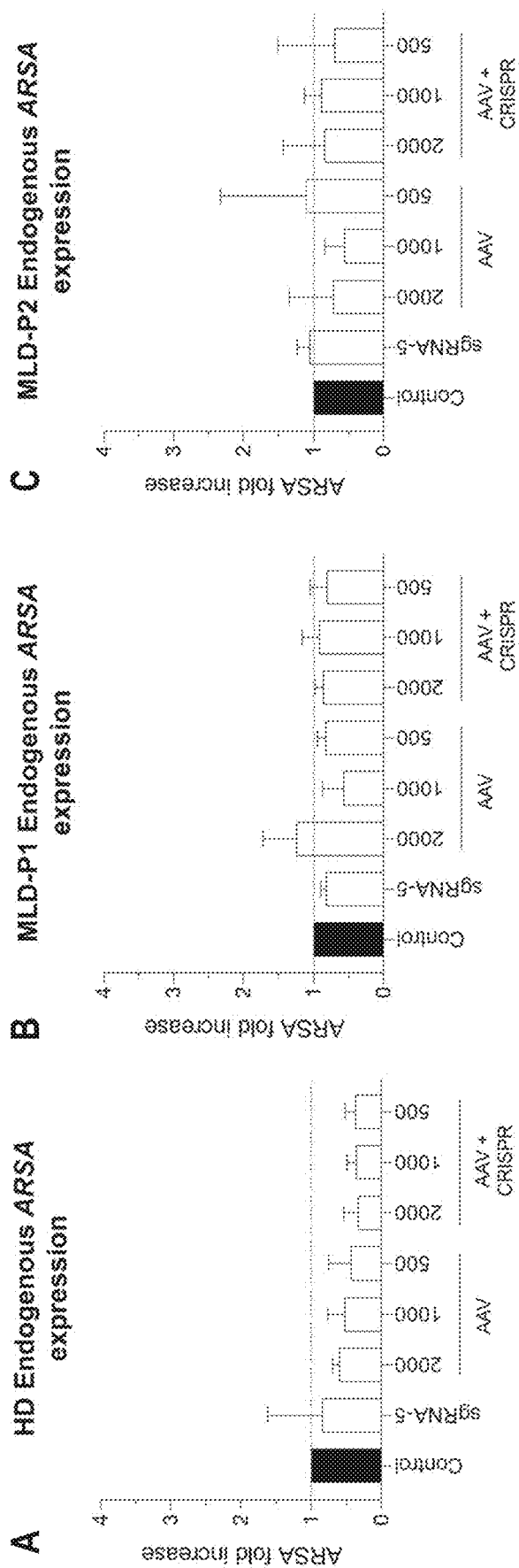
FIG. 3: Detection of endogenous ARSA mRNA by RT-qPCR after isolation of total RNA from edited myeloid-derived-suppressor cells derived from healthy donor (A), MLD patient-1 (B) and MLD patient-2 (C).

The generated data support the lack of hybridization of the designed probes to canonical ARSA mRNA. Since the cells were derived from healthy donors, the ARSA enzyme activity remained the same regardless of gene editing and correction (FIG. 2, H). The qPCR analysis to detect endogenous ARSA transcripts in cells derived from healthy donors exhibited downregulation after CRISPR treatment together with AAV transduction (60-70%) or with AAV transduction alone (40-55%; FIG. 3). In a subsequent experiment, the inventors tested whether our AAV+CRISPR treatment affected cell differentiation. Therefore, the inventors analyzed certain myeloid markers. The inventors found a similar distribution of cells expressing CD33 (range 98.6-99.5%), CD11b (37.0-39.7%), or CD66b (23.0-28.1%), irrespective of treatment (FIG. 2, I).

Proof of Concept in MLD Patient 1: Late-Infantile Phenotype with a Heterozygous Mutation (P426L/P180R)

Figure 4:
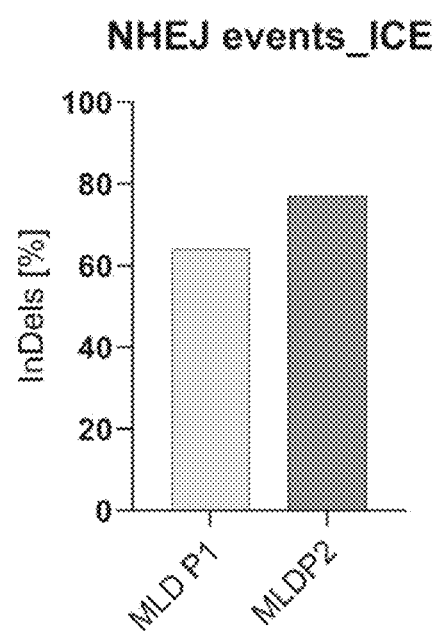
FIG. 4: ICE analysis of MLD-P1 and MLD-P2 samples to validate the gene-targeting efficacy of sgRNA-5 in HSPCs.
Figure 5:
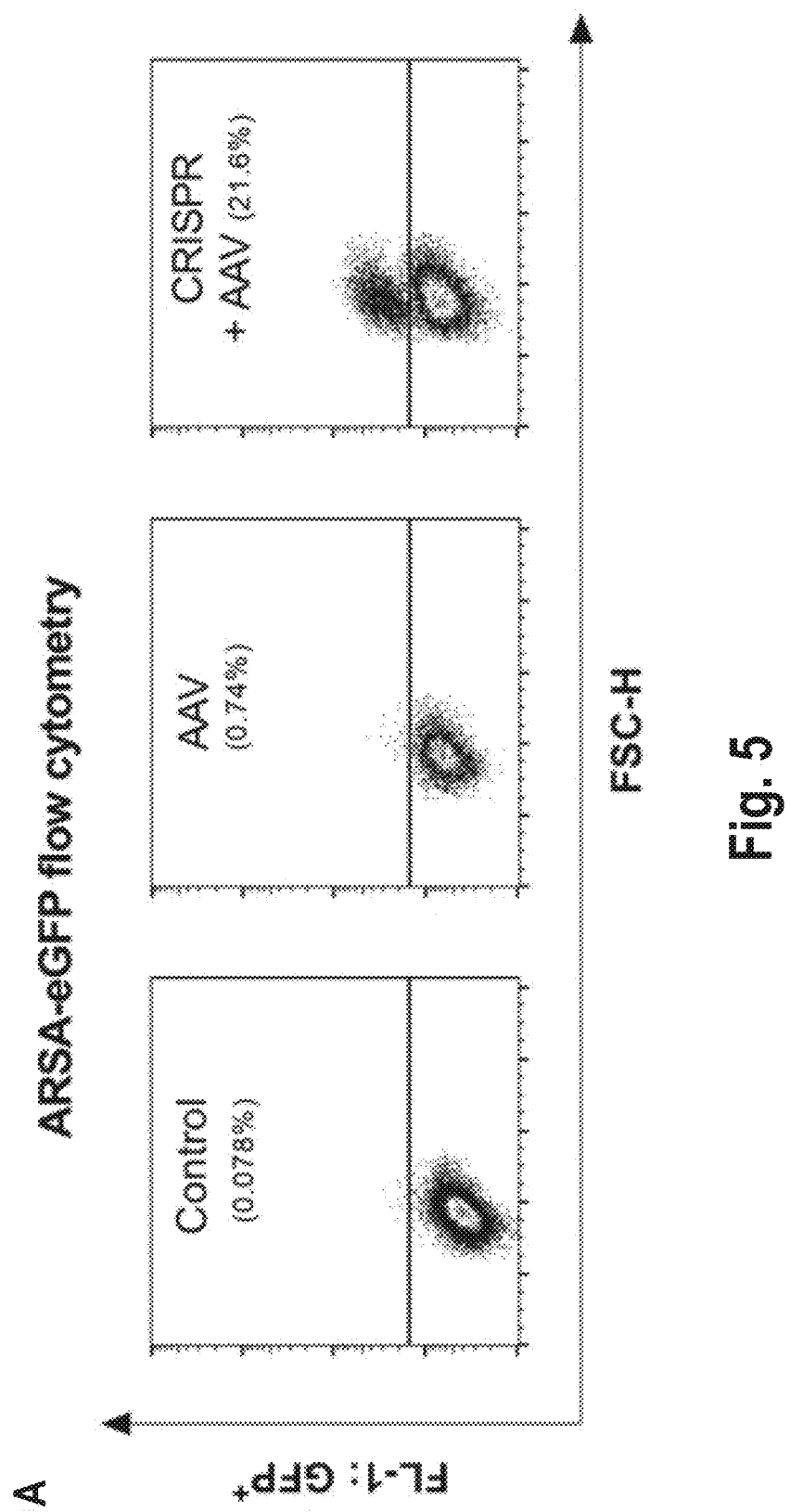
FIG. 5: Gene addition in HSPCs from a heterozygous MLD patient (P426/P180R). (A)-(D) Gene addition efficiencies using sgRNA-5 in combination with AAV-eGFP repair template at different MOI (2,000, 1,000, and 500) obtained by flow cytometry ((A) and (B)) and ddPCR ((C) and (D)). (E) Gene addition efficiency by ddPCR for the codon-optimized ARSA cDNA. (F) Cell proliferation determined 10 days post treatment for both repair templates. (G) Expression analysis for codon-optimized cDNA by qRT-PCR. (H) ARSA enzyme activity assay. Experiments were performed in triplicate.
Figure 5:
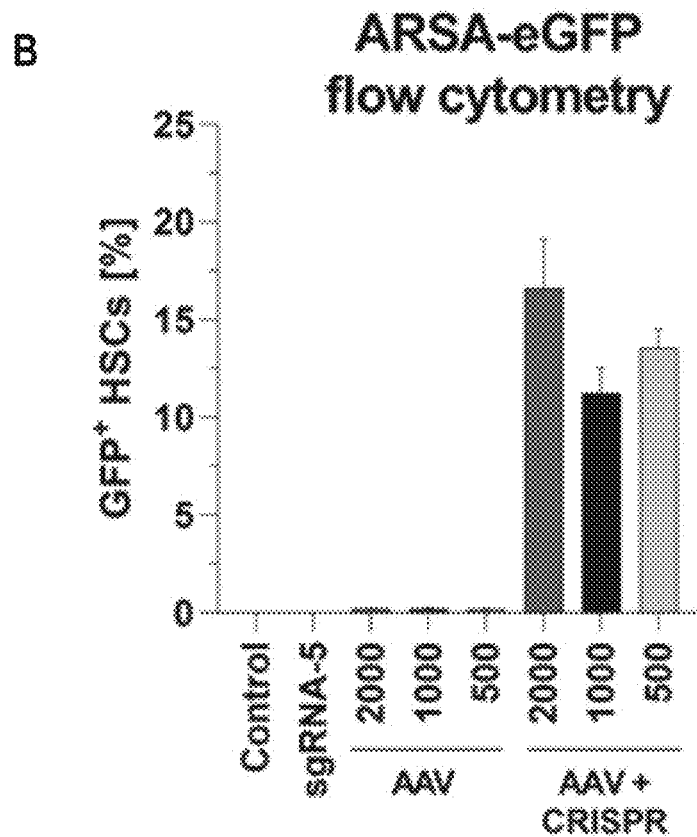
Figure 5:
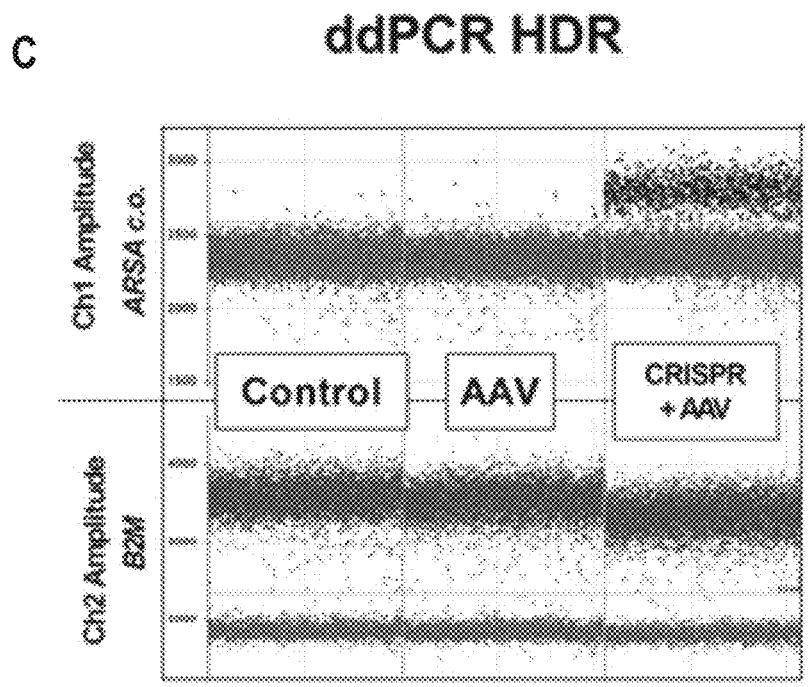
Figure 5:
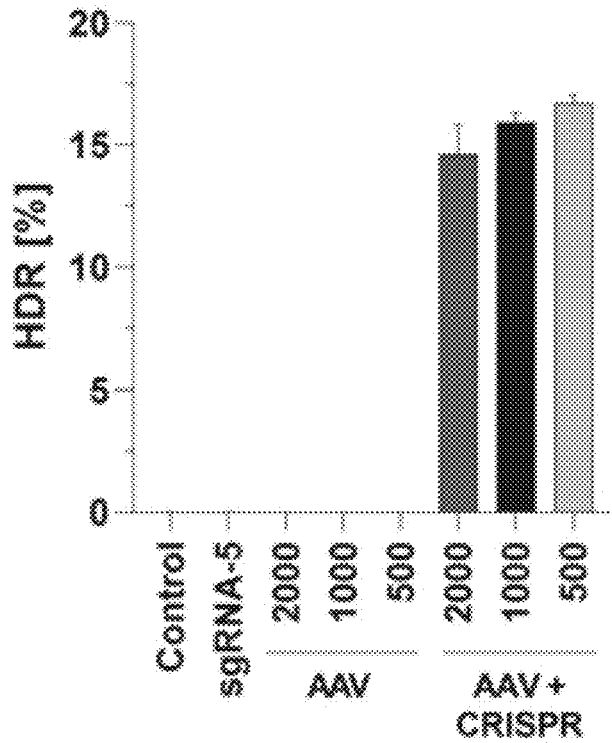
Figure 5:
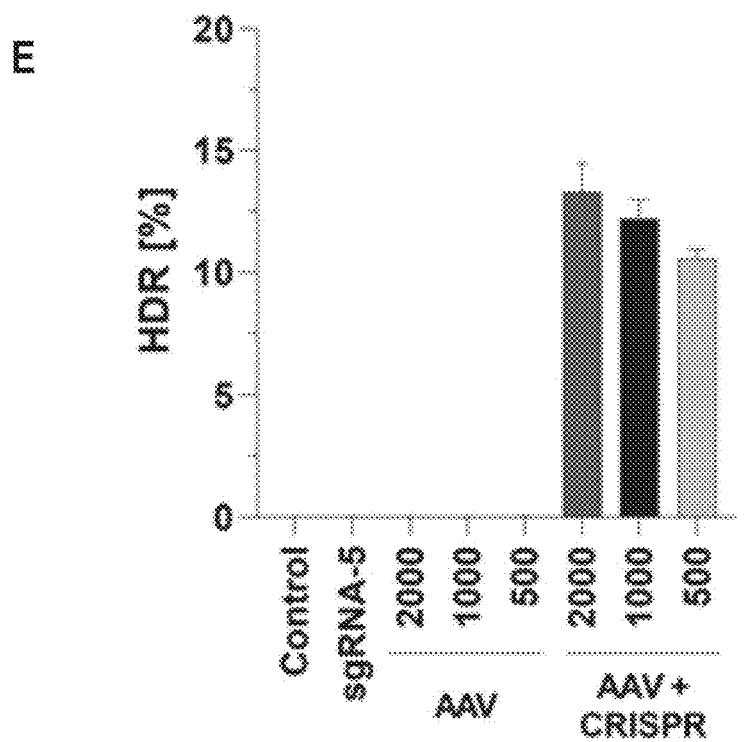
Figure 5:
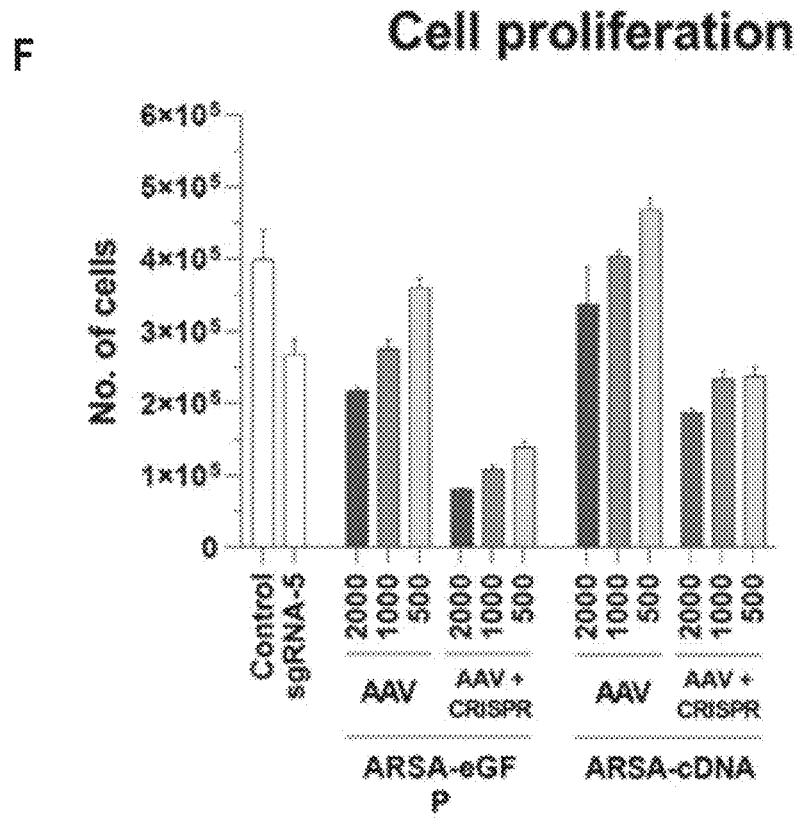
Figure 5:
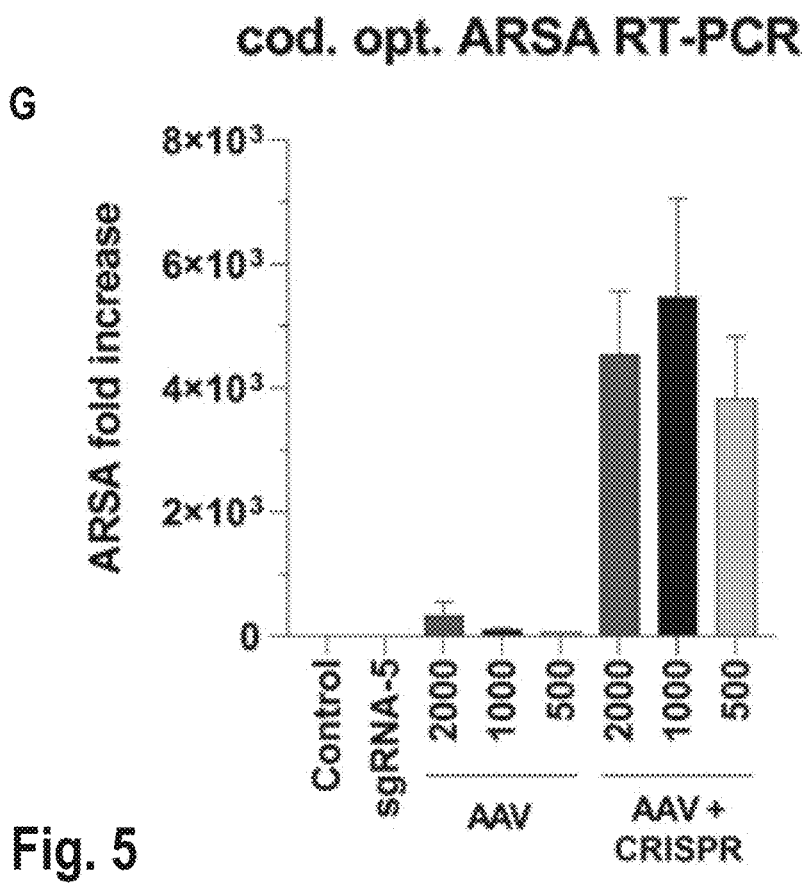
Figure 5:
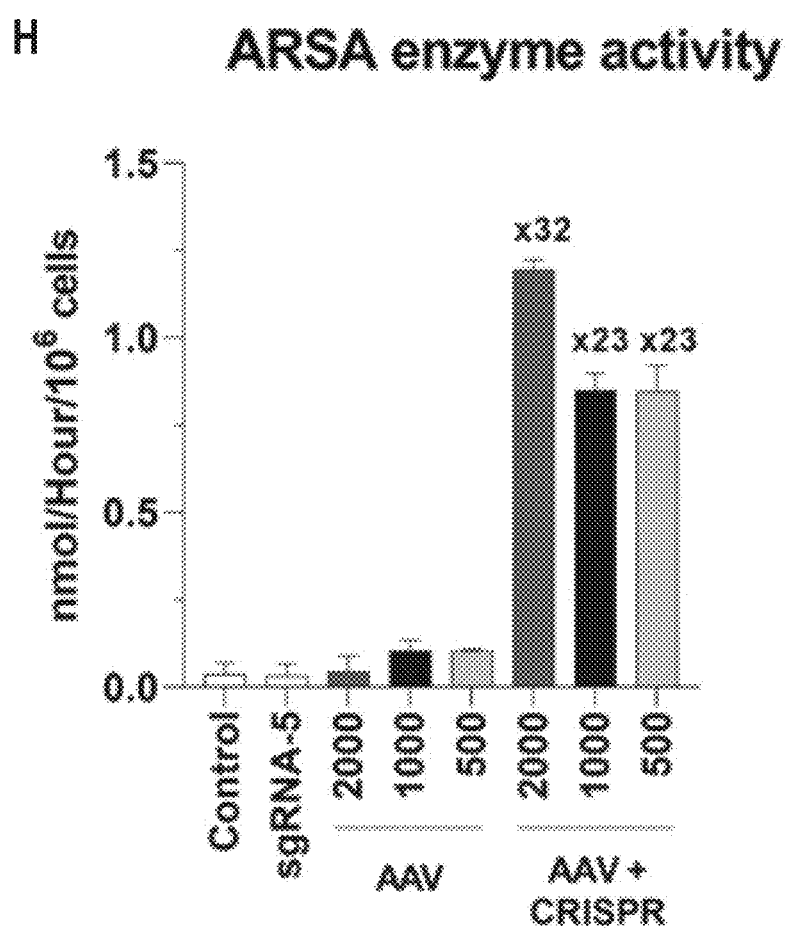

Since efficient gene integration at the targeted locus was observed in HPSCs from healthy donors, the inventors extended their analysis to HSPCs isolated from a MLD patient who carried a compound heterozygous mutation (P426L/P180R) leading to a complete loss of function of ARSA activity (at diagnosis: $0.01E/10^6$ cells). The cells were retrieved from the inventors' stem cell bank as a frozen vial and were then thawed and cultured followed by the gene integration experiment specified above. The non-homologous end joining (NHEJ) events were measured in the control sample for gene targeting and were found to be 64% (FIG. 4). The integration of eGFP transgene was found to be 16.6% at a MOI of 2,000 in flow cytometry analysis (FIGS. 5, A and B) and up to 16.7% at a MOI of 500 with ddPCR (FIGS. 5, C and D).

No dose-dependent increase in GFP$^+$ cells or signals was noted as per other MOI. In line with the eGFP transgene result, the low level of HDR efficiency using the ARSA cDNA transgene (13.3%) was observed (FIG. 5, E). A cell proliferation assay revealed that the AAV+CRISPR treatment leads to increased cellular toxicity (FIG. 5, F). However, the inventors observed >3,000-fold higher ARSA transcripts for all tested MOI in samples treated with CRISPR and AAV-ARSA cDNA compared to the untreated patient sample, but not when only AAV was applied without prior sgRNA-5-mediated gene editing (FIG. 5, G).

Very interestingly, ARSA enzyme activity measurement in treated cells revealed that the gene addition approach of the inventors was sufficient to restore ARSA activity and achieved a 32-fold induction of ARSA using an MOI of 2,000 compared to patient control samples, where other MOI attained up to 23-fold (FIG. 3, H). Remarkably, this ARSA activity was comparable to the levels of healthy myeloid-derived suppressor cells.

Proof-of-Concept in MLD Patient 2: Juvenile Phenotype with a Homozygous Mutation (P426L/P426L)

Figure 6:
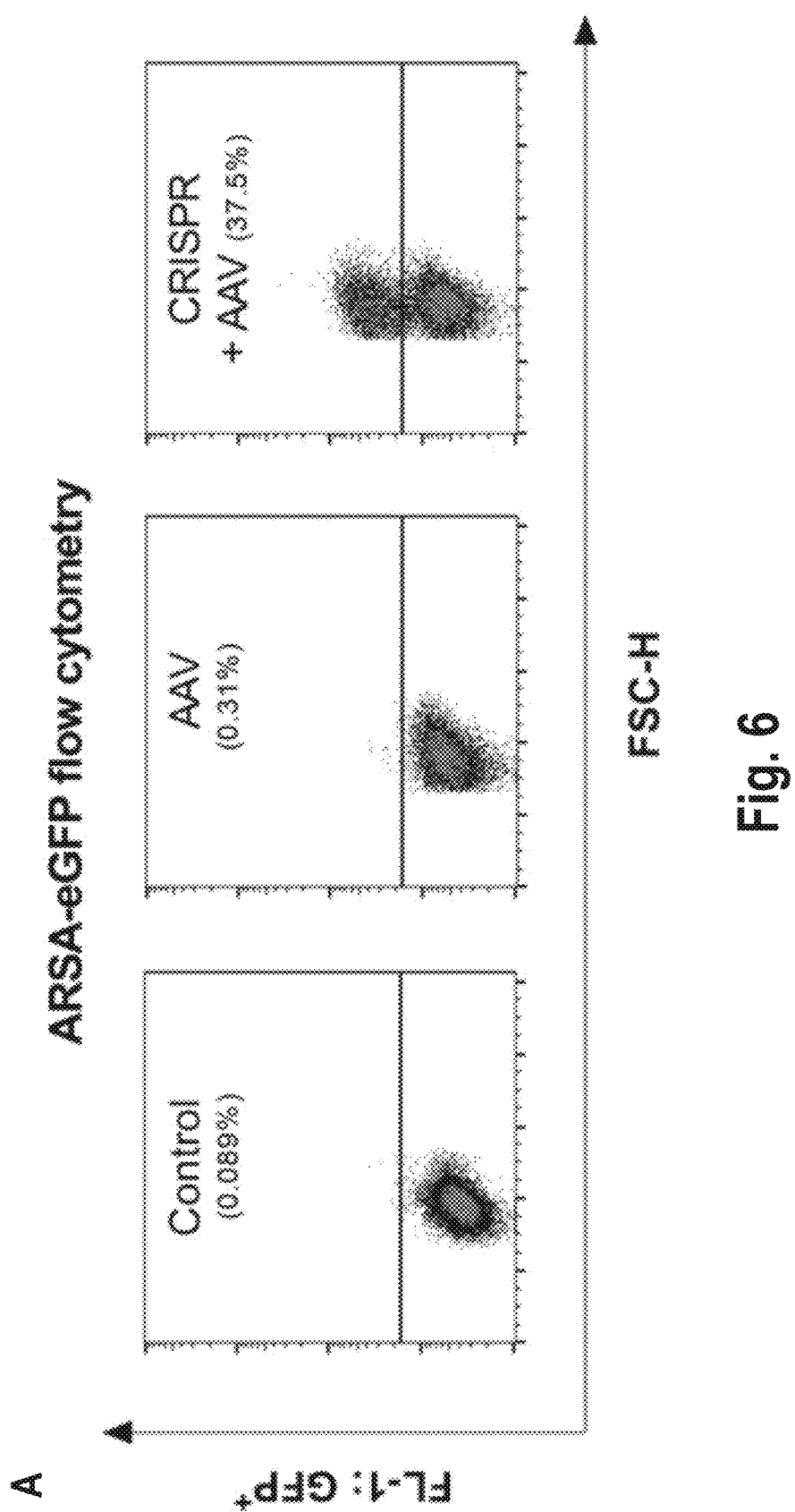
FIG. 6: Gene addition of HSPCs from a homozygous MLD patient (P426L/P426L). (A)-(D) Gene addition efficiencies using sgRNA-5 in combination with AAV-eGFP repair template at different MOI (2,000, 1,000, and 500) obtained by flow cytometry ((A) and (B)) and ddPCR ((C) and (D)). (E) Gene addition efficiency by ddPCR for the codon-optimized ARSA cDNA. (F) Cell proliferation determined 10 days post treatment for both repair templates. (G) Expression analysis for codon-optimized cDNA by qRT-PCR. (H) ARSA enzyme activity assay. Experiments were performed in triplicate.
Figure 6:
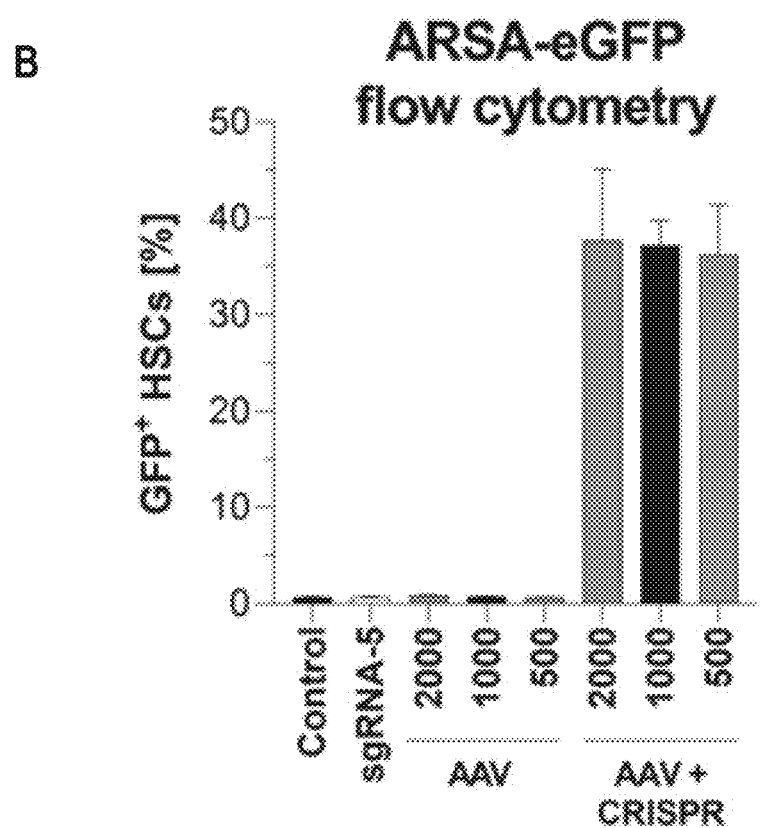
Figure 6:
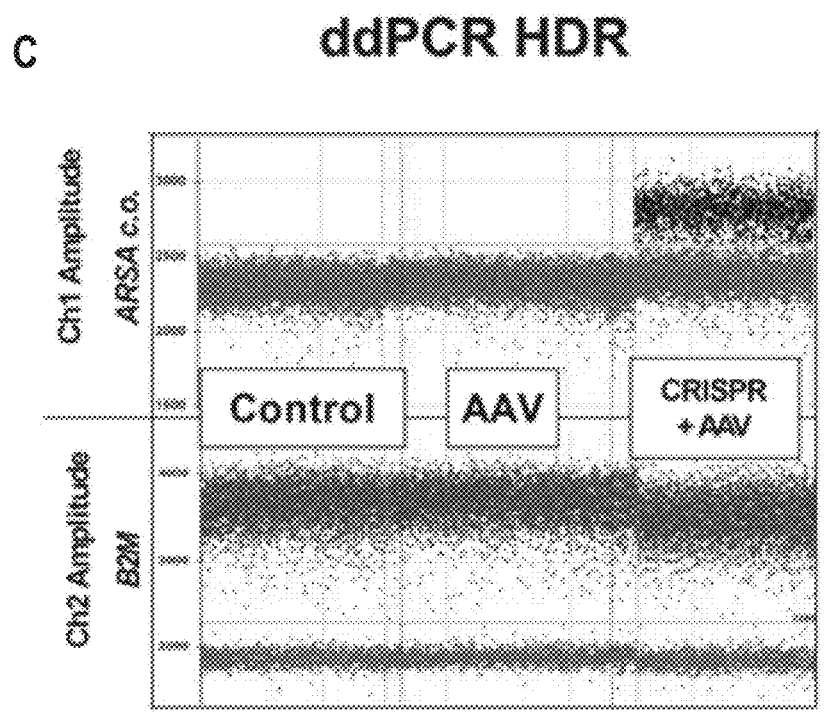
Figure 6:
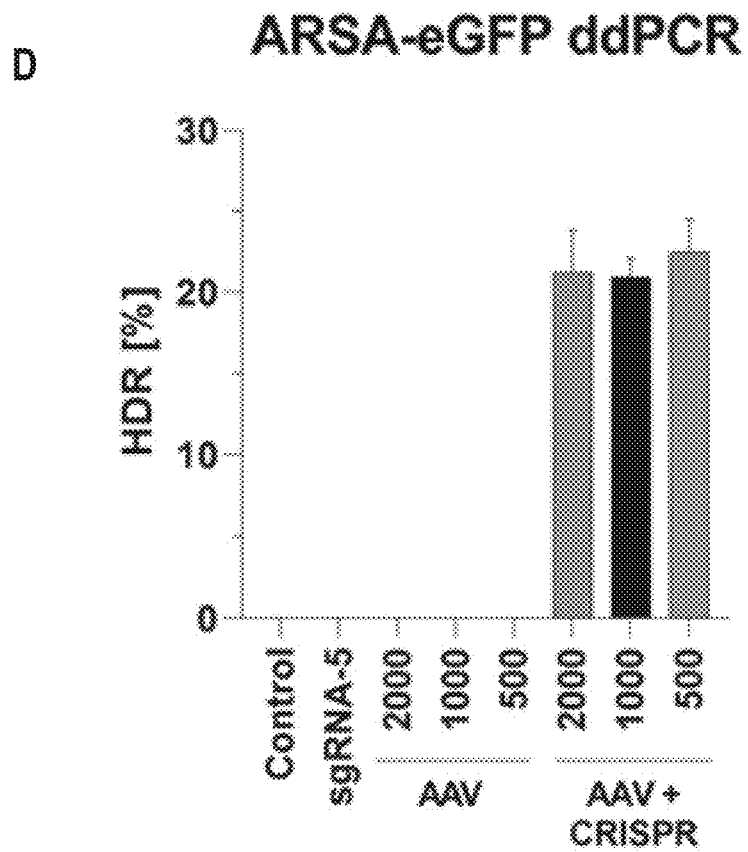
Figure 6:
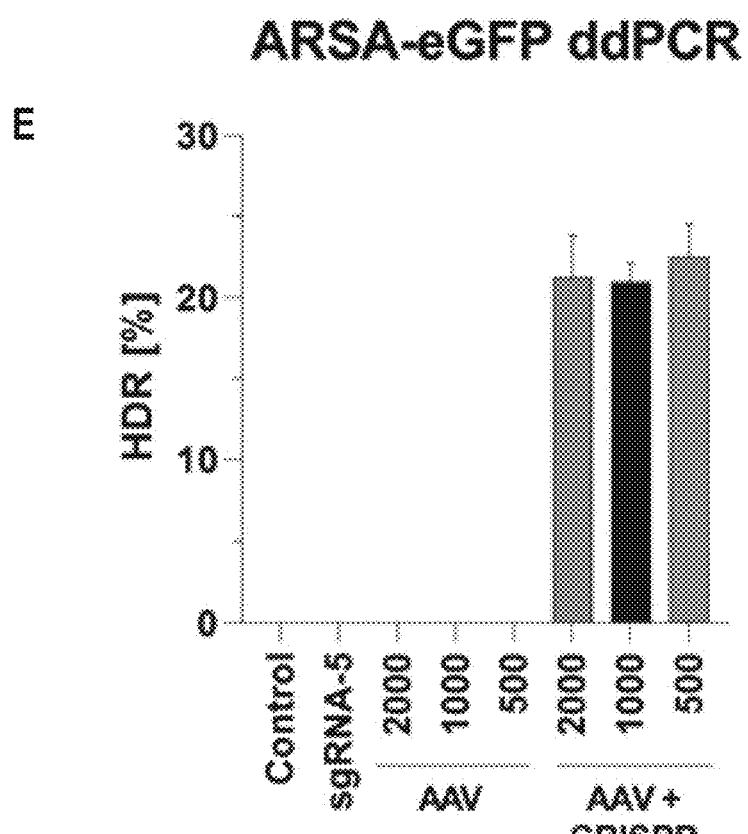
Figure 6:
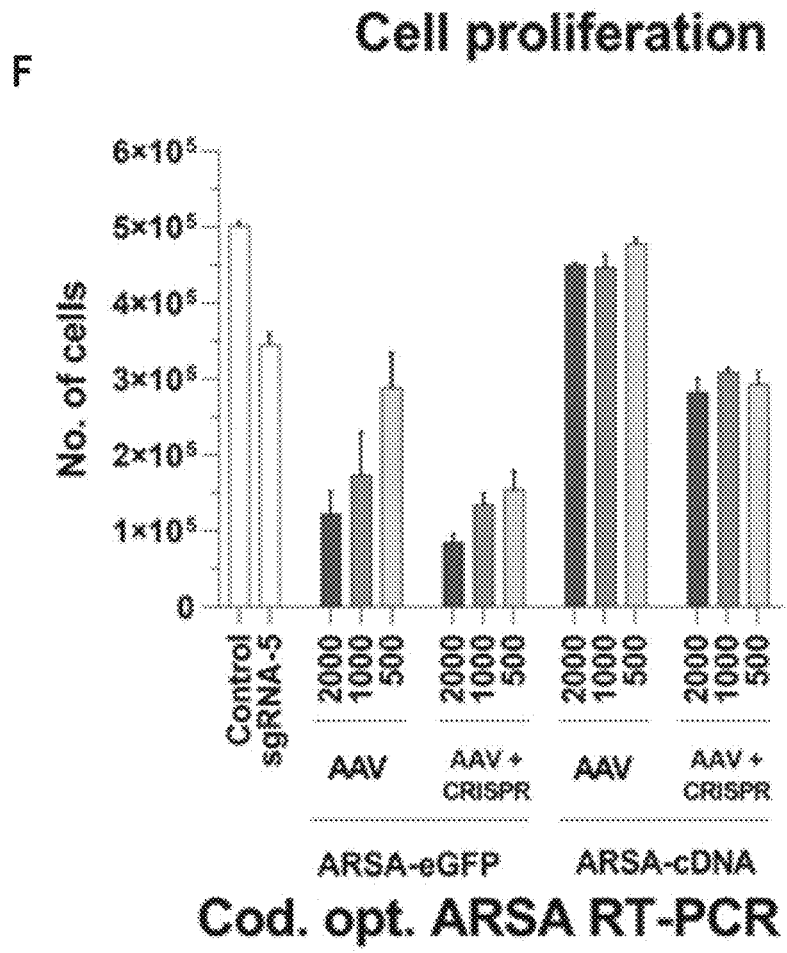
Figure 6:
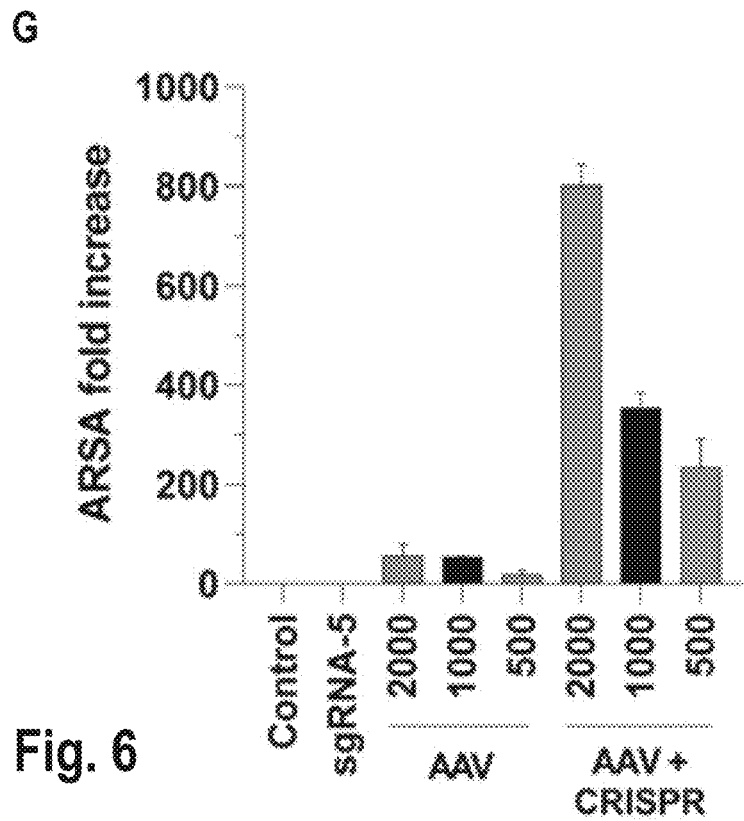
Figure 6:
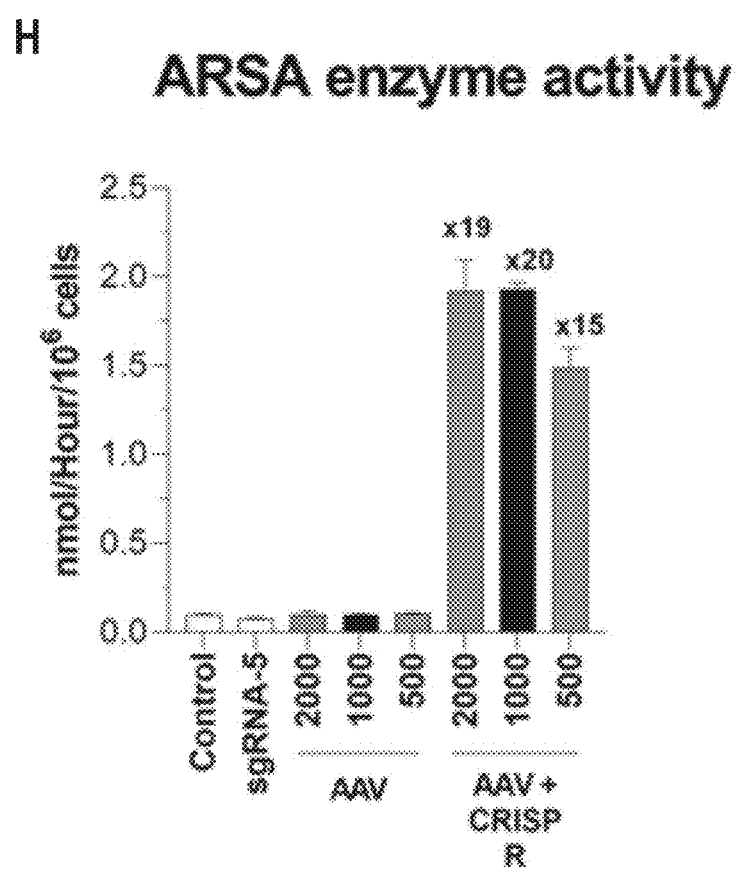

To assess the mutation-agnostic therapy further, the inventors extended their study to a homozygous MLD patient (P426L/P426L) to confirm the universality of the approach further. At the time of diagnosis, the patient showed low level of ARSA activity ($0.04E/10^6$ cells). The NHEJ events were measured in the treated sample for gene targeting verification and were found to be 77% (FIG. 4). The HDR efficiency in terms of eGFP$^+$ cells was determined by flow cytometry and found up to be 37% in the samples transduced with AAV6 (MOI of 2,000) after CRISPR treatment (FIGS. 6, A and B). The integration trend was also observed in ddPCR results, although the positive integration signal was detected only up to 22% (FIGS. 6, C and D).

The detection of ARSA cDNA transgene integration in the samples peaked at 22.9% (FIG. 6, E). The proliferation assay confirmed that electroporation and AAV transduction caused some toxicity to the treated cells (FIG. 6, F), but surprisingly, the inventors' transgene-specific qPCR analysis showed ~800-fold upregulation of ARSA mRNA expression and up to 20-fold restoration of ARSA activity in AAV-ARSA cDNA and CRISPR-treated HSPCs compared to untreated controls (FIGS. 6, G and H). The qPCR analysis to detect endogenous ARSA transcripts after transgene integration in both MLD patients did not show any distinct downregulation, as with healthy donor-derived cells, and this might be due to the low level of transgene integration (FIG. 3).

3. Conclusion

The inventors employed CRISPR-Cas9 nuclease to integrate ARSA cDNA into the endogenous ARSA locus to repair ARSA mutations as a treatment option for MLD for the very first time. Here, the inventors disclose a mutation-agnostic autologous HSPC gene therapy involving CRISPR-Cas9 and AAV6 repair template as a prospective treatment option for MLD. They experimentally proved in two MLD patient-derived cells with different mutations that their approach reconstitutes ARSA expression and improves enzyme activity (>30 fold) by inserting mutation-free ARSA cDNA precisely at the translational start site at the endogenous locus.

The inventors' strategy holds key advantages for possible MLD treatment, including: (1) a mutation-agnostic therapy that could benefit all MLD patients, since more than 200 mutations causes the disease; (2) it is safer than traditional LV-based treatments—the targeted integration of ARSA cDNA repair template at the endogenous 5' UTR locus ensures transcriptional control by natural regulatory elements with physiological ARSA expression and could potentially avoid insertional mutagenesis, unlike LV vectors; (3) the codon optimization of ARSA cDNA repair template assists the increased expression of the ARSA enzyme; and (4) the presence of SV40 poly-A region in the repair template helps to block the run-off transcription from the mutated gene after correction.

What is claimed is:

1. A gene editing system for editing the arylsulfatase A (ARSA) gene, comprising:
   (a) at least one single guide RNA (sgRNA) molecule or a nucleic acid molecule encoding said at least one gRNA, and
   (b) at least one RNA-guided endonuclease molecule or fragment thereof and/or a nucleic acid molecule encoding said at least one RNA-guided endonuclease or fragment thereof,
   wherein said sgRNA is configured to guide the RNA-guided endonuclease molecule or fragment thereof to a target region of the ARSA gene, and
   wherein said target region is within the 5' untranslated region (UTR) of the ARSA gene.

2. The gene editing system of claim 1, wherein the ARSA gene comprises at least one mutation resulting in a functional deficiency or low expression of the ARSA enzyme.

3. The gene editing system of claim 1, wherein said RNA-guided endonuclease molecule or fragment thereof, when associated with the target region, causes a double-strand break within the target region.

4. The gene editing system of claim 1, wherein said target region is within Exon 1 of the ARSA gene.

5. The gene editing system of claim 1, wherein said RNA-guided endonuclease molecule is a Cas9 molecule.

6. The gene editing system of claim 5, wherein said Cas9 is selected from the group consisting of: *Streptococcus pyogenes* Cas9 (SpCas9), *Streptococcus pyogenes* high fidelity Cas9 (HiFi SpCas9), *Streptococcus pyogenes* enhanced specificity Cas9 (eSpCas9), hyper-accurate Cas9 (HypaCas9), *Neisseria meningitides* Cas9 (Nme2Cas9), and *Staphylococcus auricularis* Cas9 (SauriCas9).

7. The gene editing system of claim 1, wherein said sgRNA molecule comprises a nucleotide sequence selected from the group consisting of SEQ ID NO:1 (sgRNA-5), SEQ ID NO:2 (sgRNA-2), SEQ ID NO:3 (sgRNA-3), SEQ ID NO:4 (sgRNA-4), and SEQ ID NO: 5 (sgRNA-1).

8. The gene editing system of claim 1 further comprising:
   (c) at least one repair template configured for the cellular expression of a functional ARSA enzyme.

9. The gene editing system of claim 7, wherein said repair template comprises a nucleotide sequence having optimized codons for an expression in mammalian cells.

10. The gene editing system of claim 7, wherein said repair template comprises the nucleotide sequence of SEQ ID NO:6 (ARSA-cDNA).

11. The gene editing system of claim 1, wherein said ARSA gene is a human ARSA gene.

12. A pharmaceutical composition comprising the gene editing system of claim 1.

13. A method of gene editing the arylsulfatase A (ARSA) gene in a cell or a subject, the method comprising contacting the cell or subject with the gene editing system of claim 1 in an amount sufficient to gene edit the ARSA gene.

14. A method of treating a disease or disorder associated with functional deficiency of the ARSA enzyme in a subject, the method comprising administering to the subject or a biological cell in the subject the gene editing system of claim 1 in an amount sufficient to gene edit the ARSA gene.

15. The method of claim 14, wherein said disease or disorder is metachromatic leukodystrophy.

* * * * *